United States Patent

Porter et al.

[11] Patent Number: 5,300,501
[45] Date of Patent: Apr. 5, 1994

[54] PEPTIDYL DERIVATIVES

[75] Inventors: John R. Porter, Slough; Thomas A. Millican; John R. Morphy, both of Maidenhead; Nigel R. A. Beeley, Thame, all of United Kingdom

[73] Assignee: Celltech Limited, Berkshire, United Kingdom

[21] Appl. No.: 916,108

[22] PCT Filed: Dec. 3, 1991

[86] PCT No.: PCT/GB91/02143
§ 371 Date: Jul. 29, 1992
§ 102(e) Date: Jul. 29, 1992

[87] PCT Pub. No.: WO90/05719
PCT Pub. Date: May 31, 1990

[30] Foreign Application Priority Data

| Dec. 3, 1990 [GB] | United Kingdom | 9026251 |
| May 13, 1991 [GB] | United Kingdom | 9110338 |
| May 13, 1991 [GB] | United Kingdom | 9110339 |
| Jun. 14, 1991 [GB] | United Kingdom | 9112888 |
| Jun. 14, 1991 [GB] | United Kingdom | 9112901 |
| Jul. 11, 1991 [GB] | United Kingdom | 9115038 |
| Jul. 11, 1991 [GB] | United Kingdom | 9115039 |
| Jul. 23, 1991 [GB] | United Kingdom | 9115916 |

[51] Int. Cl.$^5$ .......... A61K 31/185; A61K 31/535; C07C 259/06; C07D 295/15

[52] U.S. Cl. .......... 514/238.2; 514/357; 514/575; 544/168; 546/337; 562/623

[58] Field of Search .......... 544/168; 546/337; 562/623; 514/238.2, 357, 575

[56] References Cited

FOREIGN PATENT DOCUMENTS

| 0214639 | 3/1987 | European Pat. Off. |
| 0274453 | 7/1988 | European Pat. Off. |
| 90/05716 | 5/1990 | World Int. Prop. O. |
| 90/05719 | 5/1990 | World Int. Prop. O. |

*Primary Examiner*—Robert W. Ramsuer
*Attorney, Agent, or Firm*—Foley & Lardner

[57] ABSTRACT

A compound of formula (I):

$$R\underset{R^1}{\overset{R^2}{\diagdown}}\underset{O}{\overset{R^3}{\underset{R^4}{N}}}\underset{R^5}{\overset{O}{\diagup}}X \quad (I)$$

wherein
R represents a —CONHOH, carboxyl (—CO$_2$H) or esterified carboxyl group;
X represents an amino (—NH$_2$), or substituted amino, hydroxyl or substituted hydroxyl group; and their use as metalloproteinase inhibitors.

12 Claims, No Drawings

PEPTIDYL DERIVATIVES

FIELD OF THE INVENTION

This invention relates to a novel class of peptidyl derivatives, to processes for their preparation and to their use in medicine.

BACKGROUND TO THE INVENTION

In normal tissues, cellular connective tissue synthesis is offset by extracellular matrix degradation, the two opposing effects existing in dynamic equilibrium. Degradation of the matrix is brought about by the action of proteinases released from resident connective tissue cells and invading inflammatory cells, and is due, in part, to the activity of at least three groups of metalloproteinases. These are the collagenases, the gelatinases (or type-IV collagenases) and the stromelysins. Normally these catabolic enzymes are tightly regulated at the level of their synthesis and secretion and also at the level of their extracellular activity, the latter through the action of specific inhibitors, such as $\alpha_2$-macroglobulins and TIMP (tissue inhibitor of metalloproteinase), which form inactive complexes with metalloproteinases.

The accelerated, uncontrolled breakdown of connective tissues by metalloproteinase catalysed resorption of the extracellular matrix is a feature of many pathological conditions, such as rheumatoid arthritis, corneal, epidermal or gastric ulceration; tumour metastasis or invasion; periodontal disease and bone disease. It can be expected that the pathogenesis of such diseases is likely to be modified in a beneficial manner by the administration of metalloproteinase inhibitors and numerous compounds have been suggested for this purpose [for a general review see Wahl, R. C. et al Ann. Rep. Med. Chem. 25, 175-184, Academic Press Inc., San Diego (1990)].

Certain hydroxamic acid peptidyl derivatives [see for example European Patent Specifications Nos. 214639, 231081, 236872 and 274453 and International Patent Specifications Nos. WO90/05716 and WO90/05719], have been described as collagenase and/or stromelysin inhibitors.

SUMMARY OF THE INVENTION

We have now found a new class of peptidyl derivatives, members of which are metalloproteinase inhibitors and which, in particular, advantageously posses a potent and selective inhibitory action against gelatinase.

There is now much evidence that metalloproteinases are important in tumour invasion and metastasis. Tumour cell gelatinase, in particular, has been associated with the potential of tumour cells to invade and metastasise. Tumour invasion and metastasis is the major cause of treatment failure for cancer patients, and the use of a selective gelatinase inhibitor such as a compound of the present invention which is capable of inhibiting tumour cell invasion can be expected to improve the treatment of this disease.

Thus according to one aspect of the invention we provide a compound of formula (I)

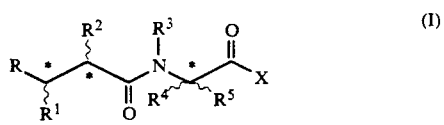

wherein R represents a —CONHOH, carboxyl (—CO$_2$H) or esterified carboxyl group;

$R^1$ represents a hydrogen atom or an optionally substituted alkyl, alkenyl, aryl, aralkyl, heteroaralkyl or heteroarylthioalkyl group;

$R^2$ represents an optionally substituted alkyl, alkenyl, cycloalkyl, cycloalkylalkyl, aryl, aralkyl, aralkoxy, or aralkylthio group, or an amino (—NH$_2$), substituted amino, carboxyl (—CO$_2$H) or esterified carboxyl group;

$R^3$ represents a hydrogen atom or an alkyl group;

$R^4$ represents a hydrogen atom or an alkyl group;

$R^5$ represents a group —[Alk]$_n$R$^6$ where Alk is an alkyl or alkenyl group optionally interrupted by one or more —O— or —S— atoms or —N(R$^7$)— groups [where R$^7$ is a hydrogen atom or a C$_{1-6}$alkyl group], n is zero or an integer 1, and R$^6$ is an optionally substituted cycloalkyl or cycloalkenyl group;

X represents an amino (—NH$_2$), or substituted amino, hydroxyl or substituted hydroxyl group;

and the salts, solvates and hydrates thereof.

It will be appreciated that the compounds according to the invention can contain one or more asymmetrically substituted carbon atoms, for example those marked with an asterisk in formula (I). The presence of one or more of these aysmmetric centres in a compound of formula (I) can give rise to stereoisomers, and in each case the invention is to be understood to extend to all such stereoisomers, including enantiomers and diastereoisomers, and mixtures, including racemic mixtures, thereof.

In the formulae herein, the ~line is used at a potential asymmetric centre to represent the possibility of R— and S— configurations, the ▬ line and the - - - line to represent an unique configuration at an asymmetric centre.

In the compounds according to the invention, when the group R represents an esterified carboxyl group, it may be for example a group of formula —CO$_2$R$^8$ where R$^8$ is a straight or branched, optionally substituted C$_{1-8}$alkyl group such as a methyl, ethyl, n-propyl, i-propyl, n-butyl, i-butyl, s-butyl or t-butyl group; a C$_{6-12}$arylC$_{1-8}$alkyl group such as an optionally substituted benzyl, phenylethyl, phenylpropyl, $\alpha$-naphthylmethyl or $\beta$-naphthylmethyl group; a C$_{6-12}$aryl group such as an optionally substituted phenyl, $\alpha$-naphthyl or $\beta$-naphthyl group; a C$_{6-12}$aryloxyC$_{1-8}$alkyl group such as an optionally substituted phenyloxymethyl, phenyloxyethyl, $\alpha$-naphthyloxymethyl or $\beta$-naphthyloxymethyl group; an optionally substituted C$_{1-8}$alkanoloxyC$_{1-8}$alkyl group, such as a pivaloyloxymethyl, propionyloxyethyl or propionyloxypropyl group; or a C$_{6-12}$aroyloxyC$_{1-8}$alkyl group such as an optionally substituted benzoyloxyethyl or benzoyloxypropyl group. Optional substituents present on the groups R$^8$ include for example one or more halogen atoms such as fluorine, chlorine, bromine or iodine atoms, or C$_{1-4}$alkyl, e.g. methyl or ethyl, or C$_{1-4}$alkoxy, e.g. methoxy or ethoxy, groups.

In general, when the group R represents as esterified carboxyl group, it may be a metabolically labile ester of a carboxylic acid.

When the groups $R^1$ and/or $R^2$ in compounds of formula (I) each represents an optionally substituted alkyl or alkenyl group, it may be, for example, a straight or branched $C_{1-6}$alkyl or $C_{2-6}$alkenyl group, such as a methyl, ethyl, n-propyl, i-propyl, n-butyl, i-butyl, s-butyl, t-butyl, n-pentyl, i-penty, n-hexyl, ethenyl, 1-propenyl, 1-butenyl or 2-butenyl group optionally substituted by one or more $C_{1-6}$alkoxy, e.g. methoxy, ethoxy, propoxy, $C_{1-6}$alkylthio, e.g. methylthio, ethylthio, propylthio, $C_{6-12}$aryl$C_{1-6}$alkoxy, e.g. phenyl$C_{1-6}$alkoxy such as benzyloxy, aralkylthio, e.g. phenyl$C_{1-6}$alkylthio such as benzylthio, amino ($-NH_2$), substituted amino, [such as $-NHR^9$, where $R^9$ is a $C_{1-6}$alkyl e.g. methyl or ethyl, $C_{6-12}$aryl$C_{1-6}$alkyl, e.g. phenyl$C_{1-6}$alkyl, such as benzyl, $C_{6-12}$aryl, e.g. phenyl, $C_{3-8}$cycloalkyl, e.g. cyclohexyl, or $C_{3-8}$cycloalkyl$C_{1-6}$alkyl, e.g. cyclohexylmethyl group], carboxyl ($-CO_2H$) or $-CO_2R^8$ [where $R^8$ is as defined above] groups.

Aryl groups represented by $R^1$ and/or $R^2$ in compounds of formula (I) include $C_{6-12}$aryl groups such as phenyl or α- or β-naphthyl groups.

Aralkyl groups represented by $R^1$ and/or $R^2$ include $C_{6-12}$aryl$C_{1-6}$alkyl groups such as phenyl$C_{1-6}$alkyl, or α- or β-naphthyl$C_{1-6}$alkyl, for example benzyl, phenylethyl, phenylpropyl, phenylbutyl, phenylpentyl, α- or β-naphthylmethyl, naphthylethyl, naphthylpropyl, naphthylbutyl or naphthylpentyl groups.

When the group $R^1$ in compounds of formula (I) is a heteroaralkyl group, it may be for example a $C_{3-6}$heteroaryl$C_{1-6}$alkyl group, such as an optionally substituted pyrrolylmethyl, furanylmethyl, thienylmethyl, imidazolylmethyl, oxazolylmethyl, thiazolylmethyl, pyrazolylmethyl, pyrrolidinylmethyl, pyridinylmethyl, pyrimidinylmethyl, morpholinylmethyl, or piperazinylmethyl group.

Heteroarylthioalkyl groups represented by $R^1$ include $C_{3-6}$heteroarylthio$C_{1-6}$alkyl groups such as optionally substituted pyrrolylthiomethyl, furanylthiomethyl, oxazolylthiomethyl, thiazolylthiomethyl, pyrazolylthiomethyl, pyrrolidinylthiomethyl, pyridinylthiomethyl, pyrimidinylthiomethyl, morpholinylthiomethyl, or piperazinylthiomethyl groups.

Optional substituents which may be present on heteroaralkyl or heteroarylthioalkyl groups represented by $R^1$ include those discussed below in relation to $R^1$ and/or $R^2$ when these groups are for example aralkyl or aralkylthioalkyl groups.

Cycloalkyl groups represented by the group $R^2$ in compounds according to the invention include $C_{3-8}$cycloalkyl groups such as cyclopentyl or cyclohexyl groups.

When $R^2$ is a cycloalkylalkyl group it may be for example a $C_{3-8}$cycloalkyl$C_{1-6}$alkyl group such as a cyclopentyl$C_{1-6}$alkyl or cyclohexyl$C_{1-6}$alkyl group, for example a cyclopentylmethyl, cyclopentylethyl, cyclopentylpropyl, cyclopentylbutyl, cyclohexylmethyl, cyclohexylethyl, cyclohexylpropyl, or cyclohexylbutyl group.

When $R^2$ is an aralkoxy or an aralkylthio group it may be for example a $C_{6-12}$aryl$C_{1-6}$alkoxy or $C_{6-12}$aryl$C_{1-6}$alkylthio group such as a phenyl$C_{1-6}$alkoxy or phenyl$C_{1-6}$alkylthio group, e.g. a benzyloxy, phenylethoxy, phenylpropoxy, phenylbutoxy, benzylthio, phenylethylthio, phenylpropylthio or phenylbutylthio group.

The cycloalkyl, cycloalkylalkyl, aryl, aralkyl, aralkoxy or aralkylthio groups represented by $R^1$ and/or $R^2$ in compounds of formula (I) may each optionally be substituted in the cyclic part of the group by one, two or more substituents [$R^{10}$] selected from halogen atoms, e.g. fluorine, chlorine, bromine or iodine atoms, or $C_{1-6}$alkyl, e.g. methyl or ethyl, $C_{1-6}$alkoxy e.g. methoxy or ethoxy, $C_{2-6}$alkylenedioxy, e.g. ethylenedioxy, halo$C_{1-6}$alkyl, e.g. tri-fluoromethyl, $C_{1-6}$alkylamino, e.g. methylamino or ethylamino, $C_{1-6}$dialkylamino, e.g. dimethylamino or diethylamino, amino ($-NH_2$), nitro, cyano, hydroxyl ($-OH$), carboxyl ($-CO_2H$), $-CO_2R^8$, where $R^8$ is as defined above, $C_{1-6}$alkylcarbonyl, e.g. acetyl, sulphonyl ($-SO_2H$), $C_{1-6}$alkylsulphonyl, e.g. methylsulphonyl, aminosulphonyl ($-SO_2NH_2$), $C_{1-6}$alkylaminosulphonyl, e.g. methylaminosulphonyl or ethylaminosulphonyl, $C_{1-6}$dialkylaminosulphonyl e.g. dimethylaminosulphonyl or diethylaminosulphonyl, carboxamido ($-CONH_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, sulphonylamino ($-NHSO_2H$), $C_{1-6}$alkylsulphonylamino, e.g. methylsulphonylamino or ethylsulphonylamino, or $C_{1-6}$dialkylsulphonylamino, e.g. dimethylsulphonylamino or diethylsulphonylamino groups. It will be appreciated that where two or more $R^{10}$ substituents are present, these need not necessarily be the same atoms and/or groups. The $R^{10}$ substituents may be present at any ring carbon atom away from that attached to the rest of the molecule of formula (I). Thus, for example, in phenyl groups any substituents may be present at the 2-, 3- or 4- 5- or 6- positions relative to the ring carbon atom attached to the remainder of the molecule.

When the group $R^2$ in compounds of formula (I) is a substituted amino group, this may be for example a group $-NHR^9$ where $R^9$ is as defined above.

Esterified carboxyl groups represented by $R^2$ include groups of formula $-CO_2R^8$ where $R^8$ is as defined above.

When the groups $R^3$ and $R^4$ in compounds of formula (I) are alkyl groups, they may be for example $C_{1-6}$alkyl groups such as methyl or ethyl groups.

When the group Alk is present in compounds of formula (I) it may be a straight or branched $C_{1-6}$alkyl, e.g. methyl, ethyl, n-propyl i-propyl, n-butyl, i-butyl, n-pentyl or n-hexyl or $C_{2-6}$alkenyl e.g. ethenyl or 1-propenyl group optionally interrupted by one or more $-O-$ or $-S-$ atoms or $-N(R^7)-$ groups where $R^7$ is a hydrogen atom or a $C_{1-6}$alkyl group such as a methyl group.

The group $R^6$ in compounds of formula (I) may represent a $C_{3-8}$cycloalkyl, e.g. cyclopentyl or cyclohexyl, or $C_{3-8}$cycloalkenyl e.g. cyclopentenyl or cyclohexenyl, group optionally substituted by one, two or more $C_{1-6}$alkyl, e.g. methyl or ethyl, $C_{1-6}$alkoxy, e.g. methoxy or ethoxy, $C_{1-6}$alkylthio, e.g. methylthio, or hydroxyl groups.

When X in the compounds of formula (I) represents a substituted amino group it may be for example a group of formula $-NR^{11}R^{12}$, where $R^{11}$ and $R^{12}$, which may be the same or different, is each a hydrogen atom (with the proviso that when one of $R^{11}$ or $R^{12}$ is a hydrogen atom, the other is not) or an optionally substituted straight or branched alkyl group, optionally interrupted by one or more $-O-$ or $-S-$ atoms or $-N(R^7)-$ or aminocarbonyloxy [$-NHC(O)O-$] groups or $R^{11}$ and $R^{12}$, together with the nitrogen atom to which they are attached, may form an optionally substituted $C_{3-6}$cyclic amino group optionally possessing one or more other heteroatoms selected from $-O-$ or $-S-$, or $-N(R^7)-$ groups.

When $R^{11}$ and/or $R^{12}$ is an alkyl group it may be for example a $C_{1-6}$alkyl group such as a methyl, ethyl, n-propyl, i-propyl, n-butyl, i-butyl, s-butyl, or —butyl group, optionally interrupted by one or more —O— or —S— atoms, or —N($R^7$)— or aminocarbonyloxy groups and may be for example a methoxymethyl, ethoxymethyl, ethoxymethyl, ethoxyethyl or ethylaminocarbonyloxymethyl group. The optional substituents which may be present on such groups include hydroxyl (—OH), carboxyl (—CO$_2$H), esterified carboxyl (—CO$_2R^8$), carboxamido (—CONH$_2$), substituted carboxamido, e.g. a group —CONR$^{11}R^{12}$ where NR$^{11}R^{12}$ is as defined herein, amino (—NH$_2$), substituted amino, for example a group of formula —NR$^{11}R^{12}$, or aryl, e.g. $C_{6-12}$aryl such as phenyl, optionally substituted by one, two or more $R^{10}$ substituents selected from those listed above in relation to the group $R^2$.

Particular examples of cyclic amino groups represented by —NR$^{11}R^{12}$ include morpholinyl, imidazolyl, piperazinyl, pyrrolyl, oxazolyl, thiazolyl, pyrazolyl, pyrrolidinyl, pyridinyl and pyrimidinyl groups.

When the group X is a substituted hydroxyl group it may be for example a group —OR$^{11}$ where R$^{11}$ is as defined above, other than a hydrogen atom.

Salts of compounds of formula (1) include pharmaceutically acceptable salts, for example acid addition salts derived from inorganic or organic acids, such as hydrochlorides, hydrobromides, hydroiodides, p-toluene sulphonates, phosphates, sulphates, perchlorates, acetates, trifluoroacetates propionates, citrates, malonates, succinates, lactates, oxalates, tartarates and benzoates.

Salts may also be formed with bases. Such salts include salts derived from inorganic or organic bases, for example alkali metal salts such as sodium or potassium salts, alkaline earth metal salts such as magnesium or calcium salts, and organic amine salts such as morpholine, piperidine, dimethylamine or diethylamine salts.

When the group R in compounds of the invention is an esterified carboxyl group, it may be a metabolically labile ester of formula —CO$_2R^8$ where R$^8$ may be an ethyl, benzyl, phenylethyl, phenylpropyl, α- or β-naphthyl, 2,4-dimethylyphenyl, 4-t-butylphenyl, 2,2,2-trifluoroethyl, 1-(benzyloxy)benzyl, 1-(benzyloxy)ethyl, 2-methyl-1-propionyloxypropyl, 2,4,6-trimethylbenzoyloxymethyl or pivaloyloxymethyl group.

In the compounds of formula (I) the group R$^1$ may in particular be a $C_{1-6}$alkyl group such as a methyl group, an aralkyl group such as benzyl group, an arylthioalkyl group such as a phenythiomethyl group or a heteroarylthioalkyl group such as thienylthiomethyl, pyridinylthiomethyl or pyrimidinylthiomethyl group or is especially a hydrogen atom.

The group R$^2$ may be in particular an optionally substituted $C_{1-6}$alkyl, $C_{3-8}$cycloalkyl, $C_{3-8}$cycloalkylC$_{1-6}$alkyl, $C_{6-12}$aryl, $C_{6-12}$arylC$_{1-6}$alkoxy or $C_{6-12}$aralkylthio group and, especially, a $C_{6-12}$arylC$_{1-6}$alkyl group. Particular types of these groups are optionally substituted $C_{3-6}$alkyl, such as n-propyl, i-propyl, n-butyl, i-butyl, s-butyl, t-butyl, n-pentyl or i-pentyl; cyclopentyl; cyclohexyl; cyclopentylC$_{1-6}$alkyl, such as cyclopentylC$_{3-6}$alkyl, e.g. cyclopentylpropyl, cyclopentylbutyl, or cyclopentylpentyl; phenyl; α- or β-naphthyl; phenylC$_{1-6}$alkoxy, e.g. phenylethoxy, phenylpropoxy or phenylbutoxy; phenylC$_{1-6}$ alkylthio, e.g. phenylethylthio, phenylpropylthio or phenylbutylthio; and, especially, phenylC$_{1-6}$alkyl such as phenylC$_{3-6}$alkyl e.g. phenylpropyl, phenylbutyl or phenylpentyl; or α- or β-naphthylC$_{1-6}$alkyl such as α- or β-naphthylC$_{3-6}$alkyl, e.g. α- or β-naphthylpropyl, naphthylbutyl or naphthylpentyl. Each of these cycloalkyl or aryl groups may be substituted, by one two or more substituents $R^{10}$ described above.

The groups $R^3$ and $R^4$ in compounds of formula (I) may each in particular be a methyl group, or, especially, a hydrogen atom.

The group $R^5$ in compounds of formula (I) may be in particular a group—AlkR$^6$, where R$^6$ is an optionally substituted cycloalkyl or cycloalkenyl group.

Thus, the group $R^5$ in compounds of formula (I) may be an optionally substituted C$_{3-8}$cycloalkylC$_{1-6}$alkyl [e.g. cyclopentylC$_{1-6}$alkyl such as cyclopentylmethyl or cyclopentylethyl, or cyclohexyC$_{1-6}$alkyl such as cyclohexylmethyl or cyclohexylethyl], C$_{3-8}$cycloalkenylC$_{1-6}$alkyl [e.g. cyclopentenylC$_{1-6}$alkyl such as cyclopentenylmethyl or cyclohexenylC$_{1-6}$alkyl such as cyclohexenylmethyl], cycloalkylC$_{1-3}$alkoxyC$_{1-3}$alkyl [e.g. cyclopentylmethoxymethyl, cyclohexylmethoxymethyl] C$_{3-8}$cycloalkenylC$_{1-3}$alkoxyC$_{1-3}$alkyl [e.g. cyclopentylmethoxymethyl or cyclohexenylmethoxymethyl] C$_{3-8}$cycloalkylC$_{1-3}$alkylthioC$_{1-3}$alkyl [e.g. cyclopentylmethylthiomethyl or cyclohexylmethylthiomethyl] or C$_{3-8}$cycloalkenylC$_{1-3}$alkylthioC$_{1-3}$alkyl [e.g. cyclopentenylmethylthiomethyl or cyclohexenylmethylthiomethyl], C$_{3-8}$cycloalkyC$_{1-3}$alkylaminoC$_{1-3}$alkyl [e.g. cyclopentylmethylaminomethyl, or cyclohexylmethylaminomethyl] or C$_{3-8}$cycloalkenylC$_{1-3}$alkylaminoC$_{1-3}$alkyl [e.g. cyclopentenylmethylaminomethyl or cyclohexenylmethylaminomethyl] group.

The group X in compounds of formula (I) may be in particular an amino (—NH$_2$) or —NR$^{11}R^{12}$ group. Particular —NR$^{11}R^{12}$ groups are —NHR$^{12}$ groups.

Groups of this type include those where R$^{12}$ is a C$_{1-6}$alkyl group, for example a methyl, ethyl, or n-propyl group, optionally interrupted by one or more —O— or —S— atoms or —N(R$^7$) [e.g. —NH— or —N(CH$_3$)—] or aminocarbonyloxy groups and optionally substituted by a hydroxyl, carboxyl, carboxyalkyl, e.g. carboxymethyl, carboxamido, amino, —NR$^{11}R^{12}$, [for example di-C$_{1-6}$alkylamino such as dimethylamino, C$_{1-6}$alkylamino such as methylamino, or C$_{3-6}$ cyclic amino such as morpholinyl, pyrrolidinyl or pyridinyl] or phenyl optionally substituted by one, two or more R$^{10}$ substituents.

A particularly useful group of compounds according to the invention is that of formula (I) wherein R$^5$ is a AlkR$^6$, group, where Alk is a C$_{1-6}$ alkyl and R$^6$ is a cycloalkyl or cycloalkenyl group.

Another particularly useful group of compounds according to the invention is that of formula (I) where R$^2$ is an optionally substituted alkyl, cycloalkyl, cycloalkylalkyl, aryl, aralkoxy or aralkylthio group.

A further particularly useful group of compounds of formula (I) are those wherein X is an amino or substituted amino group.

In general, in compounds of formula (I) the groups R$^1$, R$^3$ and R$^4$ is each preferably a hydrogen atom.

In a further preference, the group R in compounds according to the invention is a —CONHOH or a —CO$_2$H group or a metabolically labile ester thereof. In a particular preference, however, R is a —CONHOH or a —CO$_2$H group An especially useful group of compounds according to the invention has the formula (Ia)

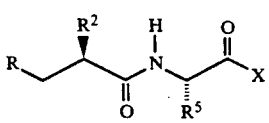

(Ia)

wherein R, $R^2$, $R^5$ and X are as defined for formula (I); and the salts, solvates and hydrates thereof.

A particularly useful group of compounds of formula (Ia) are those wherein R represents a —CONHOH or —$CO_2$H group; $R^2$ represents an optionally substituted alkyl, alkenyl, cycloalkyl, cycloalkylalkyl, aryl, aralkoxy or aralkythio group;

$R^5$ represents a group —AlkR$^6$, where Alk is a $C_{1-6}$alkyl group and $R^6$ is a cycloalkyl or cycloalkenyl group;

X is an amino (—$NH_2$) or substituted amino group; and the salts, solvates and hydrates thereof.

Particularly useful compounds of formula (Ia) are those wherein $R^5$ is a group —AlkR$^6$, and $R^6$ is an optionally substituted cyclohexyl group. Compounds of this type in which $R^5$ is a cyclohexyl$C_{1-6}$alkyl group, particularly a cyclohexylmethyl group, are especially useful.

Other useful compounds of formula (Ia) include those wherein $R^2$ represents a $C_{3-6}$alkyl group, particularly an iso-butyl or n-pentyl group, or a cycloalkyl$C_{3-6}$alkyl group, particularly a cyclohexylpropyl, cyclohexylbutyl or cyclohexylpentyl group, or especially an optionally substituted phenyl$C_{2-6}$alkyl group particularly an optionally substituted phenylethyl phenylpropyl, phenylbutyl or phenylpentyl group. Optional substituents on the phenyl group may be one, two or more $R^{10}$ groups as defined for compounds of formula (I).

In the compounds of formula (Ia) X may be a —$NH_2$ group or a group—$NR^{11}R^{12}$ as defined for compounds of formula (I).

An especially useful group of compounds according to the invention has the formula (Ia) wherein $R^2$ is an optionally substituted phenyl$C_{3-6}$alkyl group, especially an optionally substituted phenypropyl or phenylbutyl group, $R^5$ is a cyclohexylmethyl group; and X is a amino (—$NH_2$) or $NR^{11}R^{12}$ group. Compounds of this type wherein X is —$NH_2$ or —$NHR^{12}$ are particularly useful.

In the compounds of formulae (I) and (1a), when the group $R^5$ is a cycloalkyl$C_{1-6}$alkyl group then the chiral centre to which this group is attached preferably has a S-configuration.

Particularly preferred compounds according to the invention include:

[4-(N-Hydroxyamino)-2(R)-cyclohexylmethylsuccinyl]-L-β-cyclohexylalanine-N-(2-phenylethyl) amide;

[4-N-(Hydroxyamino)-2R-isobutylsuccinyl]-L-β-cyclohexylalanine-N-(2-phenylethyl) amide

[4-(N-hydroxyamino)-2R-phenylpropylsuccinyl]-L-β-cyclohexylalanine-N-(2-phenylethyl) amide

[4-(N-Hydroxyamino)-2R-phenylpropylsuccinyl]-L-β-cyclohexylalanine-N-[2-(N,N-dimethylamino] amide

[4-(N-Hydroxyamino)-2R-phenylpropylsuccinyl]-L-β-cyclohexylalanine-N-(2-(p-sulphonamidophenyl)ethyl) amide

[4-(N-Hydroxyamino)-2R-phenylpropylsuccinyl]-L-β-cyclohexylalanine-N-(2-(p-sulphonylphenyl) ethyl) amide

[4-(N-Hydroxyamino)-2R-phenylpropylsuccinyl]-L-β-cyclohexylalanine-N-[(2-(2-pyridyl)-ethyl] amide

[4-(N-Hydroxyamino)-2R-pentylsuccinyl]-L-β-cyclohexylalanine-N-(2-phenylethyl) amide

[4-(N-Hydroxyamino)-2R-isoamylsuccinyl]-L-β-cyclohexylalanine-N-(2-phenylethyl) amide

[4-(N-Hydroxyamino)-2R-phenylbutylsuccinyl]-L-β-cyclohexylalanine-N-(2-phenylethyl) amide

[4-(N-Hydroxyamino)-2R-phenylpropylsuccinyl]-L-β-cyclohexylalanine-N-[3-(4-(morpholimyl propyl)] amide

[4-(N-Hydroxyamino)-2R-phenylpropylsuccinyl]-L-β-cyclohexylalanine-N-[β-(alanine methyl ester] amide

[4-(N-Hydroxyamino)-2R-phenylpropylsuccinyl]-L-β-cyclohexylalanine-N-[β-alanine]amide.

[4-(N-Hydroxyamino)-2R-isobutylsuccinyl]-L-β-cyclohexylalanine amide

[4-(N-Hydroxyamino)-2R-(3-phenylpropyl)succinyl]-L-β-cyclohexylalanine amide

[4-(N-Hydroxyamino)-2R-(3-phenylbutyl)succinyl]-L-β-cyclohexylalanine amide

[4-Hydroxy-2(R)-(3-phenylpropyl)succinnyl]-L-β-cyclohexylalanine-(N-2-phenylethyl) amide

[4-Hydroxy-2(R)-(3-phenylpropyl)succinyl]-L-β-cyclohexylalanine-β-alanine methyl ester

[4-Hydroxy-2(R)-(3-phenyl propyl)succinyl]-L-β-cyclohexylalanine-β-alanine

[4-Hydroxy-2(R)-(3-phenylpropyl)succinyl]-L-β-cyclohexylalanine-β-alanine amide

[4-Hydroxy-2(R)-isobutylsuccinyl]-L-β-cyclohexylalanine-(N-2-phenylethyl) amide

[4-Hydroxy-2(R)-isoamylsuccinyl]-L-β-cyclohexylalanine-(N-2-phenylethyl) amide

[4-Hydroxy-2(R)-[3(4-methylphenyl)propyl]succinyl]-L-β-cyclohexylalanine-N-(2-phenylethyl) amide

[4-Hydroxy-2R-phenylpropylsuccinyl]-L-β-cyclohexylalanine-N-[2-(benzyloxycarbomyl)ethyl] amide

[4-Hydroxy-2R-phenylpropylsuccinyl]-L-β-cyclohexylalanine-N-[2-(p-sulphonamidophenyl) ethyl] amide

[4-Hydroxy-2R-phenylpropylsuccinyl]-L-β-cyclohexylalany glycine methyl ester

Compounds of general formula (I) may be prepared by any suitable method known in the art and/or by the following process.

It will be appreciated that where a particular stereoisomer of formula (I) is required, the synthetic processes described herein may be used with the appropriate homochiral starting material and/or isomers may be resolved from mixtures using conventional separation techniques e.g. hplc Thus for example a compound of formula (I) with S stereochemistry at the chiral centre adjacent to the substituent $R^5$ may be prepared using an appropriate homochiral starting material and the techniques described in the Examples.

Thus in a second aspect the invention provides a process for preparing a compound of formula (I) in which —$CO_2R$ is —$CO_2H$ may be prepared from a corresponding ester of formula (I) using conventional procedures, depending on the nature of the ester group. Thus, for example, a compound of formula (I) may be prepared by hydrolysis of the corresponding ester, using for example an acid or base optionally in a solvent.

Thus for example a compound of formula (I) with S stereochemistry at the chiral centre adjacent to the substituent $R^5$ may be prepared using an appropriate homochiral starting material and the techniques described in the Examples.

The compounds according to the invention may be prepared by the following processes. In the description and formulae below the groups R, $R^1$, $R^2$, $R^3$, $R^4$, $R^5$ and X are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable amino or hydroxyl protecting groups include benzyl, benzyloxycarbonyl or t-butyloxycarbonyl groups. These may be removed from a protected derivative by catalytic hydrogenation using for example hydrogen in the presence of a metal catalyst, for example palladium on a support such as carbon in a solvent such as an alcohol e.g. methanol, or by treatment with trimethylsilyl iodide or trifluoroacetic acid in an aqueous solvent. Suitable carboxyl protecting groups include benzyl groups, which may be removed from a protected derivative by the methods just discussed, or alkyl groups, such as a t-butyl group which may be removed from a protected derivative by treatment with trifluoroacetic acid in an aqueous solvent. Other suitable protecting groups and methods for their use will be readily apparent. The formation of the protected amino, hydroxyl or carboxyl group may be achieved using standard alkylation or esterification procedures, for example as described below.

Thus according to a further aspect of the invention a compound of formula (I) may be prepared by coupling an acid of formula (II)

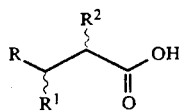 (II)

or an active derivative thereof, with an amine of formula (III)

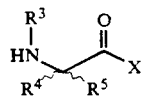 (III)

followed by removal of any protecting groups.

Active derivatives of acids for formula (II) include for example acid anhydrides, or acid halides, such as acid chlorides.

The coupling reaction may be performed using standard conditions for amination reactions of this type. Thus, for example the reaction may be achieved in a solvent, for example an inert organic solvent such as an ether, e.g. a cyclic ether such as tetrahydrofuran, an amide e.g. a substituted amide such as dimethylformamide, or a halogenated hydrocarbon such as dichloromethane at a low temperature, e.g. $-30°$ C. to amibient temperature, such as $-20°$ C. to $0°$ C., optionally in the presence of a base, e.g. an organic base such as an amine, e.g. triethylamine or a cyclic amine such as N-methylmorpholine. Where an acid of formula (II) is used, the reaction may additionally be performed in the presence of a condensing agent, for example a diimide such as N,N'-dicyclohexylcarbodiimide, advantageously in the presence of a triazole such as I-hydroxybenzotriazole. Alternatively, the acid may be reacted with a chloroformate for example ethylchloroformate, prior to reaction with the amine of formula (III).

Free hydroxyl or carboxyl groups in the starting materials of formulae (II) [where R is —CONHOH or $CO_2H$] and (III) may need to be protected during the coupling reaction. Suitable protecting groups and methods for their removal may be those mentioned above.

It will be appreciated that where a particular steroisomer of formula (I) is required, this may be obtained by resolution of a mixture of isomers following the coupling reaction of an acid of formula (II) and an amine of formula (III). Conventional resolution techniques may be used, for example separation of isomers by Chromatography e.g. by use of high performance liquid chromatography. Where desired, however, appropriate homochiral starting materials may be used in the coupling reaction to yield a particular stereo isomer of formula (I). Thus, in particular process a compound of formula (Ia) may be prepared by reaction of a compound of formula (IIa)

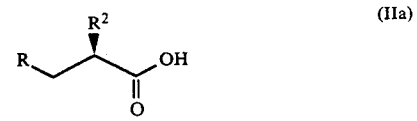 (IIa)

with an amine of formula (IIIa)

 (IIIa)

as described above

Intermediate acids of formula (II) wherein R is a carboxyl or esterified carboxyl group may be prepared by hydrolysing a corresponding ester of formula (IV)

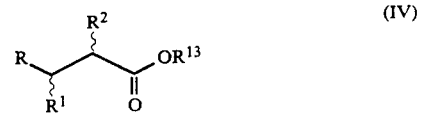 (IV)

where $R^{13}$ is an alkyl group, for example a methyl or t-butyl group, using for example trifluoroacetic acid, or, when $R^{13}$ is a methyl group using enzymatic hydrolysis, such as for example with α-chymotrypsin, in an aqueous solvent. In this reaction, enzymatic hydrolysis (for example as more particularly described in the Examples herein) usefully provides a method of isomer selection.

The ester of formula (IV) may be prepared by esterification of the corresponding acid of formula (V)

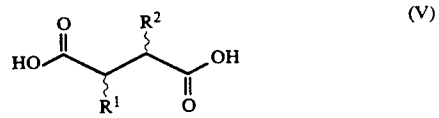 (V)

using an appropriate acyl halide, for example an acyl chloride in a solvent such as an alcohol, e.g. methanol at a low temperature, e.g. around $0°$ C.

Acids of formula (V) may be prepared by alkylation of a compound of formula (VI)

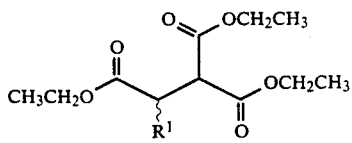 (VI)

with an appropriate halide, e.g. a compound R²Hal, where Hal is a halogen atom such as a chlorine or bromine atom in the presence of a base, for example an alkoxide such as sodium ethoxide in a solvent such as an alcohol, e.g. ethanol at ambient temperature, followed by decarboxylation using for example concentrated hydrochloric acid at an elevated temperature, e.g. the reflux temperature.

Intermediates of formula (VI) are either known compounds or may be prepared by methods analogous to those used for the preparation of the known compounds.

Intermediate acids of formula (IV) wherein R is a —CONHOH group or a protected derivative thereof may be prepared by reaction of an anhydride of formula (VII)

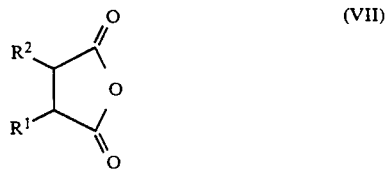 (VII)

with a hydroxylamine such as O-benzylhydroxylamine in a solvent such as tetrahydrofuran at a low temperature, e.g. around −20° C., followed where desired by removal of the protecting group as described above.

The intermediate anhydrides of formula (VII) may be prepared for example by heating for example at the reflux temperature, a diacid of formula (V) where R is —CO₂H with an acyl chloride such as acetyl chloride.

The homochiral acids of formula (IIa) may be prepared according to another feature of the invention by oxidation of an oxazolidinone of formula (VIII)

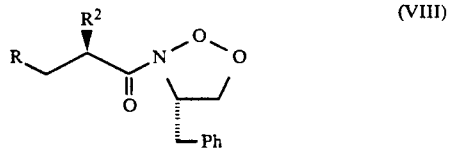 (VIII)

(where Ph is a phenyl group)
using an oxidizing agent such as peroxide, e.g. hydrogen peroxide in a solvent such as an ether e.g. a cyclic ether such as tetrahydrofuran, at a low temperature, e.g. around 0° C. followed by treatment with a base, such as lithium hydroxide, at an elevated temperature.

The compounds of formula (VIII) are novel, particularly useful, intermediates for the preparation of stereoisomers of formula (Ia) and form a further aspect of the invention.

The compounds of formula (VIII) may be prepared by reaction of an acyl halide RCH₂CH(R²)COHal (where Hal is a halogen atom such as chloride, bromine or iodine atom) with a solution of (S)-4-(phenylmethyl)-2-oxazolidinone in the presence of a base such as n-butyl lithium in a solvent such as tetrahydrofuran at a low temperature, e.g. around −78° C.

Acyl halides RCH₂CH)(R²)COHal may be prepared by treatment of the corresponding known acids RCH₂CH(R²)CO₂H with conventional halogenating agents for example thionyl halides under standard reaction conditions.

In another process according to the invention, a compound of formula (I) where R is a carboxyl group may be prepared by decarboxylation of a corresponding compound of formula (IX).

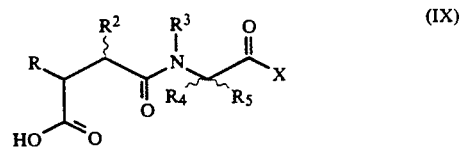 (IX)

The reaction may be achieved using standard conditions, for example by heating a compound of formula (IX) in an inert solvent, such as an aromatic hydrocarbon, e.g. xylene, at the reflux temperature.

The intermediate acids of formula (IX) may be prepared by reaction of a protected acid of formula (X)

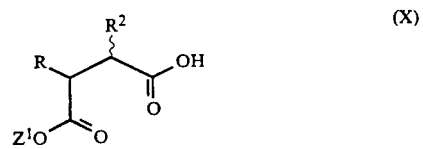 (X)

where R is a protected carboxyl group such as a benzyloxycarbonyl group and Z¹ is a protecting group such as a benzyl group with an amine of formula (III) using reagents and conditions as described above for coupling compounds of formula (II) and (III), followed by removal of the protecting groups.

The intermediates of formula (X) may be prepared by treatment of an appropriate malonic ester RCH₂CO₂Z¹ with a halide of formula (XI)

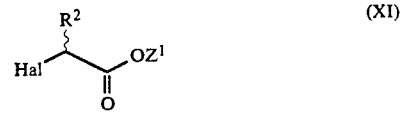 (XI)

(where Hal is a halogen atom, e.g. a chlorine or bromine atom) in the presence of a base such as potassium t-butoxide in a solvent such as dimethylformamide at ambient temperature.

Halides of formula (XI) may be prepared by halogenation and subsequent decarboxylation of a di-acid of formula (XII).

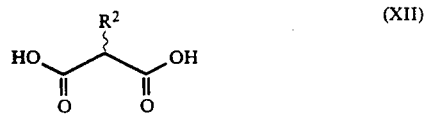 (XII)

using for example a halogenating agent such as bromine in a solvent such as diethyl ether at ambient temperature, followed by heating of the resulting halogenated intermediate in a solvent such as an aromatic hydrocarbon e.g. xylene, at the reflux temperature.

Intermediates of formula (XII) may be prepared by hydrolysis of the corresponding di-alkylester (e.g. the dimethyl or diethyl ester using a base such as sodium or potassium hydroxide in a solvent such as an alcohol e.g. methanol at the reflux temperature. The di-alkyl ester starting materials are either known compounds or may be prepared by methods analogous to those used for the preparation of the known compounds, for example as described in the Examples herein.

Compounds of formula (I) may also be prepared by interconversion of other compounds of formula (I). Thus, for example, a compound of formula (I) wherein R is a —CONHOH group may be prepared by reaction of a corresponding acid of formula (I) wherein R is a —CO$_2$H group or an active derivate thereof (for example an acid chloride or an acid anhydride) with hydroxylamine or an O-protected derivative or a salt thereof. The reaction may be performed using the reagents and conditions described above in the preparation of compounds of formula (I) from the starting materials of formulae (II) and (III).

In another interconversion process, compounds of formula (I) wherein R is —CO$_2$H and/or X contains a —CO$_2$H group may be prepared by hydrolysis of the corresponding esterified compounds (for example where R is a —CO$_2$R$^8$ group and/or X contains a similar group) using conventional procedures, for example by treatment with a base, e.g. an alkali metal hydroxide such as lithium hydroxide in a solvent such as an aqueous alcohol, e.g. aqueous methanol, or by treatment with an acid such as a mineral acid, e.g. hydrochloric acid in the presence of a solvent, e.g. dioxan.

Similarly esters of formula (I), for example where R is a CO$_2$R$^8$ group and/or X contains a —CO$_2$R$^8$ group may be prepared by reaction of the corresponding acids, where R is a —CO$_2$H group and/or X contains a —CO$_2$H group or an active derivative thereof, with an alcohol R$^8$OH using standard conditions.

The compounds according to the invention are potent and selective inhibitors of gelatinase. The activity and selectivity of the compounds may be determined by the use of appropriate enzyme inhibition test for example as described in Example A hereinafter. In our tests using this approach, compounds according to the invention have been shown to inhibit gelatinase with Ki values in the picomolar-nanomolar range and to have around a 40 fold or greater selectivity for gelatinase over stromelysin, and around a 20-fold or greater selectivity for gelatinase over collagenase.

The ability of compounds of the invention to prevent tumour cell invasion may be demonstrated in a standard mouse model.

Thus, briefly, nude mice may be inoculated with a tumour cell line showing gelatinase-dependent invasion and the ability of compounds according to the invention to reduce subsequent lung tumour colonisation may be evaluated in accordance with standard procedures. In out tests, compounds according to the invention, when administered intravenously at 1 mg/kg to mice in the above model have reduced lung tumour colonisation to negligable levels.

The compounds according to the invention can be expected to be of use to prevent tumour cell metastasis and invasion. The compounds may therefore be of use in the treatment of cancer, particularly in conjunction with radiotherapy, chemotherapy or surgery, or in patients presenting with primary tumours, to control the development of tumour metastasises. Thus, according to a further aspect of the invention we provide a compound of formula (I) for use in the treatment of cancer to control the development of tumour metastasises. Particularly cancers may include breast, melanoma, lung, head, neck or bladder cancers.

For use according to this aspect of the invention, the compounds of formula (I) may be formulated in a conventional manner, optionally with one or more physiologically acceptable carriers, diluents or excipients.

Thus according to a further aspect of the invention we provide a pharmaceutical composition comprising a compound of formula (I) and a pharmaceutically acceptable diluent, carrier or excipient.

In a still further aspect the invention provides a process for the production of a pharmaceutical composition comprising bringing a compound of formula (I) into association with a pharmaceutically acceptable diluent, carrier or excipient.

Compounds for use according to the present invention may be formulated for oral, buccal, parental or rectal administration or in a form suitable for nasal administration or administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles; and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of formula (I) may be formulated for parental administration by injection e.g. by bolus injection or continuous infusion. Formulations for injection may be presented in unit dosage form. The compositions for injection may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of formula (I) may also be formulated in rectal compositions such as suppositories or retention enemas, e.g. containing conventional suppository bases such as cocoa butter or other glycerides.

In addition to the formulations described above the compounds of formula (I) may also be formulated as a depot preparation. Such long acting formulations may be administered by implantation or by intramuscular injection.

For nasal administration or administration by inhalation the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas.

The compositions may, if desired, be presented in a pack or dispenser device which may contain one or more unit dosage forms containing the active ingredient. The pack or dispenser device may be accompanied by instructions for administration.

The doses of compounds of formula (I) used to control the development of tumour metastasises will vary depending on the condition of the patient to be treated but in general may be in the range around 0-5 mg to 50 mg/kg body weight, particularly from about 1 mg to 40 mg/kg body weight. Dosage units may be varied according to the route of administration of the compound in accordance with conventional practice.

DESCRIPTION OF SPECIFIC EMBODIMENTS

The invention is further illustrated in the following non-limiting Examples.

In the Examples, the following abbreviations are used:

| | |
|---|---|
| RT | room temperature |
| DCCI | N,N'-dicyclohexylcarboiimide |
| DMF | dimethylformamide |
| THF | tetrahydrofuran |
| TFA | trifluoroacetic acid |
| RPHPLC | reverse phase high performance liquid chromatography |
| HOBT | N-hydroxybenzotriazole |

EXAMPLE 1

[4-(N-hydroxyamino)-2(R)-cyclohexylmethylsuccinyl]-L-β-cyclohexylalanine-N-(2-phenylethyl) amide (I)

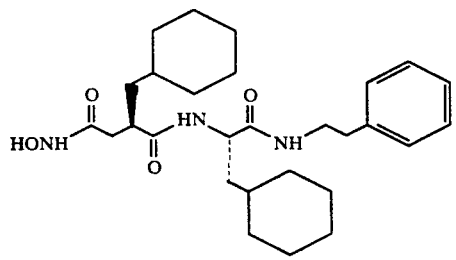

(R,S)-Cyclohexylmethyl succinic acid

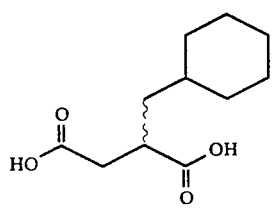

C

Sodium ethoxide was prepared by adding sodium metal (2.5 g, 108 mmoL) to anhydrous ethanol (150 ml) under nitrogen. Triethyl 1,1,2-ethanetricarboxylate (26.6 g, 25 ml, 108 mmoL) was added and the mixture stirred at room temperature for 20 minutes. Cyclohexylmethyl bromide (19.12 g, 15 ml, 108 mmoL) was added dropwise over 1 hour and the solution raised to reflux overnight. The precipitated sodium bromide was filtered off and the filtrate concentrated in vacuo. The residue was treated with cold $H_2O$ (200 ml) and extracted with diethyl ether (3×100 ml). The organic layer was dried ($Na_2SO_4$) and concentrated to give a clear oil. (32.2 g). Concentrated hydrochloric acid (200 ml) was added to the crude tricarboxylate (32.2 g) and the mixture brought to reflux. After 96 hours the reaction was cooled and poured into $CH_2Cl_2$ (200 ml) and extracted. The organic layer was dried ($Na_2SO_4$) to give the diacid C a white solid (16.0 g)

$^1$H NMR ($CDCL_3$) δ 0.85 (m, 2H), 1.2 (m, 5H), 1.65 (m, 6H), 2.5 (dd, 1H, J=4 and 16 HZ) 2.70 (dd, 1H, J=9 and 16 HZ), 2.95 (m, 1H).

(R,S) Dimethyl cyclohexylmethyl succinate D

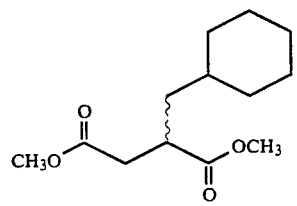

Acetyl chloride (4.33 g, 3.9 ml, 55.2 mmoL) was added to anhydrous methanol (50 ml) at 0° C. and the reaction stirred for 15 min. The reaction was allowed to come to the diacid C (5.0 g, 23.3 mmoL) added. Following a 3 hour reflux the reaction was cooled and concentrated in vacuo to give a clear oil which was taken up in ethyl acetate (200 ml), washed with saturated sodium bicarbonate, brine, and dried ($Na_2SO_4$). The solution was evaporated to dryness to afford the diester D as an oil (5.45 g).

$^1$H NMR ($CDCL_3$) δ 0.85 (m, 2H), 1.2 (m, 6H), 1.65 (m, 5H), 2.42 (dd, 1H, J=6.0 Hz and 16 HZ) 2.70 (dd, 1H, J=10.0 and 16 HZ), 2.95 (m, 1H), 3.68 (s, 3H), 2.7 (s, 3H).

Methyl (R)-2-Cyclohexylmethyl succinate E

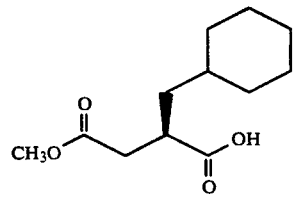

A solution of α-chymotrypsin (635 mg) in $H_2O$ (20 ml) was treated with compound D (5.23 g, 21.6 mmoL) in $H_2O$ (75 ml). A constant pH of 7.8 was maintained by titrating the reaction mixture with 0.1M NaOH using a pH-stat.

After 24 hours the solution was washed with diethyl ether and the aqueous layer acidified to pH=2.0 with 1.0M HCL. The resultant solution was concentrated in vacuo to dryness. The residue was sonicated in the presence of diethyl ether and filtered. The ether layer was washed with brine, dried (Na₂SO₄) and concentrated to give the acid E as a clear oil (2.0 g).

¹H NMR (CDCL₃) δ 0.9 (m, 2H), 1.25 (m, 6H), 1.65 (m, 5H), 2.42 (dd, 1H, J=5.5 and 17 HZ) 2.70 (dd, 1H, J=8 and 17 HZ), 2.95 (m, 1H), 3.7 (s, 3H)

Methyl(R)-2-Cyclohexylmethyl-succinyl-L-β-cyclohexylalanine-N-(2-phenylethyl) amide (F)

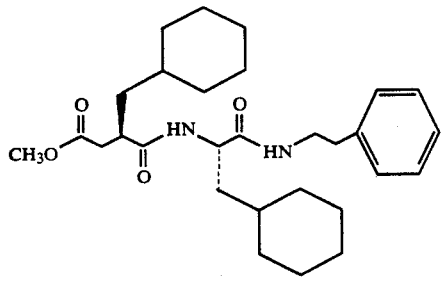

To a solution of the acid E (338 mg, 1.48 mmoL) in dry CH₂Cl₂ (20 ml) was added 4-nitrophenol (227 mg, 1.63 mmoL) and DCCl (336 mg, 1.63 mmoL). After 1 hour the reaction was filtered, concentrated and dissolved in dry DMF (5 ml). L-β-cyclohexylalanine-N-(2-phenylethyl) amide J (359 mg, 1.63 mmoL) in dry DMF (5 ml) was added and the reaction left overnight at 60° C. DMF was removed in vacuo, and the residue dissolved in CH₂CL₂ and poured into NaHCO₃ (aq). The organic layer was washed with 0.1M HCl and dried (Na₂SO₄). The residue was concentrated in vacuo and purified on silica gel (Merck 9385) using CH₂Cl₂/MeOH 95:5 to give 500 mg of F.

¹H NMR (CDCl₃) δ 0.9 (m, 4H), 1.2 (m, 12H), 1.65 (m, 10H), 2.65 (m, 5H), 3.5 (m, 2H), 3.7 (s, 3H), 4.4 (m, 1H), 6.15 (d, 1H), 6.35 (m, 1H), 7.25 (m, 5H).

[4-Hydroxy-2R-cyclohexylmethylsuccinyl]-L-β-cyclohexylalanine-N-(2-phenylethyl) amide G

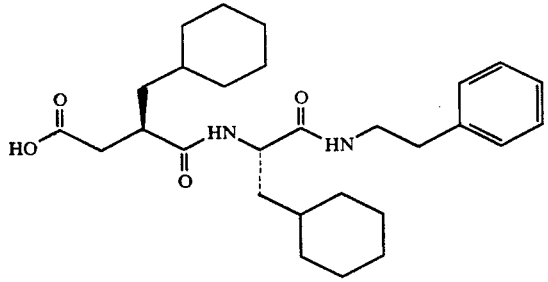

The ester F (250 mg, 0.5 mmoL) in 1,4-dioxan (3 ml) was added to 1.5M HCl (3 ml). A further 2 ml of 1,4-dioxan was added to obtain solution. The reaction was left at 50° C. overnight. A further 1.0 ml of 1.5M HCl was added followed by 1.0 ml of 1,4-dioxan and the reaction left a further 6 hours at 50° C. The solvent was removed in vacuo, the residue dissolved in CH₂Cl₂ and purified on silica gel (Merck 9385) using CH₂Cl₂/MeOH 9:1 to give G as a clear oil (117 mg).

¹H NMR (CDCl₃) δ 0.95 (m, 4H), 1.2 (m, 12H), 1.8 (m, 10H), 2.5 (m, 2H), 2.85 (m, 2H), 3.1 (2H, m), 3.5 (m, 1H), 4.45 (m, 1H)

[4-(N-Benzyloxyamino)-2R-Cyclohexylmethylsuccinyl]-L-β-cyclohexylalanine-N-(2-phenylethyl) amide H

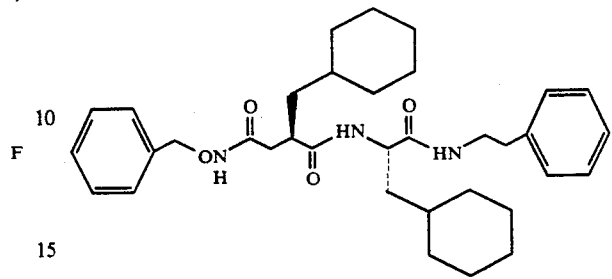

The acid G (117 mg, 0.25 mmoL) was dissolved in dry THF (10 ml) and cooled to −20° C. Ethylchloroformate (27 mg, 0.25 mmoL) and N-methylmorpholine (25 mg, 0.25 mmoL) were added and the mixture stirred at −20° C. for 1 hour. O-Benzylhydroxylamine (30.25 mg, 0.25 mmoL) was added and the reaction allowed to come to room temperature. Following an overnight reaction, the volatiles were removed under reduced pressure and the residue mixed with diethyl ether. A precipitate formed, the ether was decanted and the residue dissolved in methanol. The product (100 mg) was shown to be homogenous on hplc (DYNAMAX C18 eluting with TFA/H₂O/CH₃CN (starting with 0.1:80:20 ending with 0.1:0:100 over 20 min).

[4-(N-Hydroxyamino)-2R-cyclohexylmethyl succinyl]-L-β-cyclohexylalanine-N-(2-phenylethyl) amide I Compound H (100 mg) was dissolved in MeOH (20 ml) and hydrogenolysed using 5% Pd-C and hydrogen gas. After 1 hour at RT the catalyst was removed by filtration and the product purified on RPHPLC using TFA/H₂O/CH₃CN (starting with 0.1:80:20 ending with 0.1:0:100 over 20 min) to give the title compound I (60 mg).

¹H NMR (CD₃OD) δ 8.1–8.2 (1H, m), 7.1–7.4 (5H, m), 4.3–4.45 (1H, m), 3.4–3.5 (2H, m), 2.7–2.9 (3H, m), 2.40 (1H, dd), 2.30 (1H, dd), 0.8–2.0 (26H, m)

L-β-cyclohexylalanine-N-(2-phenylethyl) amide (J)

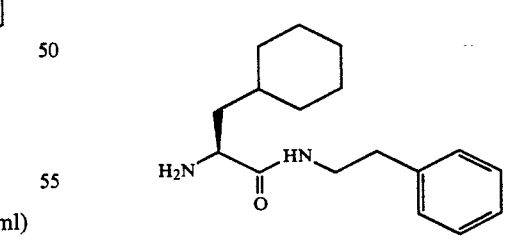

tBoc-β-cyclohexyl-L-alanine (1.35 g, 5 mmoL) was dissolved in dry CH₂Cl₂. 4-Nitrophenol (695 mg, 5 mmoL) was added followed by DCCl (1.03 g, 5 mmoL). After 1 hour at room temperature the reaction was concentrated in vacuo, ether was added and the solution filtered. The residue was concentrated in vacuo, dissolved in CH₂Cl₂ (10 ml) and phenethylamine (690 μl, 5.5 mmoL) was added. The reaction was poured into NaHCO₃ and extracted with CH₂Cl₂ (3×20 ml), was dried (Na₂SO₄) and concentrated in vacuo.

Purification on silica gel (Merck 9385) using CH₂Cl₂→CH₂Cl₂/MeOH 85:15) gave a clean oil (900 mg) which was dissolved in CH₂Cl₂/TFA (9:1) and left a RT for 30 min. The reaction was concentrated in vacuo, dissolved in CH₂Cl₂ (50 ml) and poured into Na₂CO₃ (aq). The organic layer was separated, dried (Na₂SO₄) and concentrated in vacuo to give an oil which was purified on silica gel (Merck 9385) using CH₂Cl₂/MeOH/NEt₃ 96:3:1 to give the title compound J as an oil (500 mg).

¹H NMR (CDCL₃) δ 0.95 (m, 2H), 1.25 (m, 6H), 1.55 (bs, 2H), 1.65 (m, 5H), 2.8 (t, 2H, J=6 HZ), 3.4 (dd, 1H, J=3 and 10 HZ), 3.5 (dd, 2H, J=6 and 12 HZ), 7.2 (m, 5H)

EXAMPLE 2

[4-N-(Hydroxyamino)-2R-isobutylsuccinyl]-L-β-cyclohexylalanine-N-(2-phenylethyl) amide R,S-Isobutylsuccinic acid    K

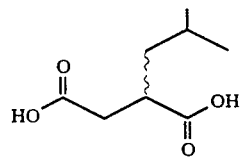

Sodium ethoxide was prepared by adding sodium metal (2.5 g, 108 mmoL) to anhydrous ethanol (150 ml) under nitrogen. Triethyl 1,1,2-ethanetricarboxylate (26.6 g, 25 ml, 108 mmoL) was added and the mixture stirred at room temperature (RT) for 20 minutes. Isobutyl bromide (19.12 g, 15 ml, 108 mmoL) was added dropwise over 1 hour and the solution raised to reflux overnight. The precipitated sodium bromide was filtered off and the filtrate concentrated in vacuo. The residue was treated with cold H₂O (200 ml) and extracted with diethyl ether (3×100 ml). The organic layer was dried (Na₂SO₄) and concentrated to give a clear oil (32.2 g) which was refluxed with concentrated hydrochloric acid for 96 hours. On cooling, a white crystalline solid precipitated which was filtered, washed with ice cold water and dried in vacuo to give the title compound K (11.0 g)

¹HNMR (CDCL₃) δ 0.85 (3H, d, J=6 Hz), 0.90 (3H, d, J=6 Hz), 1.3-1.45 (1H, m), 1.55-1.75 (2H, m), 2.50 (1H, dd, J=6 and 18 Hz), 2.70 (1H, dd, J=9 and 18 Hz), 2.85-2.95 (1H, m).

3-(R,S)-Isobutylsuccinic anhydride    L

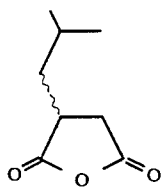

The diacid K (10.21 g, 59 mmoL) was treated with acetyl chloride (27 ml, 376 mmoL) under reflux for 2½ hours. Volatiles were removed under reduced pressure to give the anhydride L (9.37 g, 100%) as a brownish oil.

¹HNMR (CDCL₃) 0.95 (3H, d, J=6 Hz), 1.05 (3H, d, J=6 Hz), 1.48-1.90 (3H, m), 2.65 (1H, dd, J=7 and 18 Hz), 3.10 (1H, dd, J=9 and 18 Hz), 3.15-3.25 (1H, m).

[4-(N-Benzyloxyamino)-2R,S-Isobutyl] succinic acid M

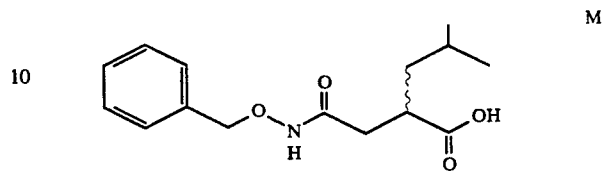

O-Benzyl hydroxylamine (7.8 g, 63.4 mmoL) in dry THF (50 ml) was added dropwise (over 1 hour) to a solution of the anhydride L (9.37 g, 60.0 mmoL) in dry THF (100 ml) at −20° C. After stirring a further 1 hour, volatiles were removed in vacuo and the residue taken up in ethyl acetate. After washing with 1.0 MHCL (×3), the organic phase was dried (MgSO₄) and evaporated to give a white solid. The crude solid was dissolved in hot diethyl ether and filtered. Colourless crystals of the acid M deposited on standing (6.7 g, 41%).

¹HNMR (CDCL₃) δ 0.8-1.0 (6H, m), 1.2-1.4 (3H, m), 2.1-2.4 (2H, m), 2.8-3.0 (1H, m), 4.85 (2H, s), 7.3 (5H, bs), 8.6 (1H, bs).

[4-(N-Benzyloxyamino)-2R,S-Isobutyl succinyl]-L-β-cyclohexylalanine-N-(2-phenylethyl) amide    N

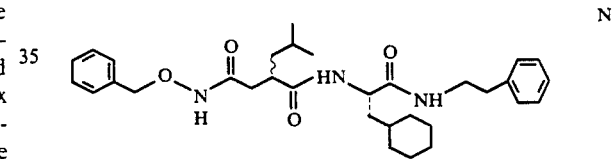

The acid M (502 mg, 1.8 mmoL) was dissolved in dry THF (20 ml) and cooled to −20° C. Ethylchloroformate (245 mg, 233 μl, 1.8 mmoL) and N-methyl morpholine was added and the suspension left for 1 hour at −20° C. A DMF solution (10 ml) of L-β-Cyclohexylalanine-N-(2phenylethyl)amide J (500 mg, 1.8 mmoL) was added dropwise. Once the addition was completed the cooling bath was removed and the reaction allowed to warm up to room temperature overnight. The organic solution was poured into 10% HCl and extracted with ethyl acetate (×3). The organic layer was dried (MgSO₄) and concentrated in vacuo to give a solid. Purification on silica gel (Merck 9385) using CH₂Cl₂/MeOH 98:2 gave the title compound N as a mixture of diastereoisomers (200 mg).

¹HNMR (CDCL₃) 0.7-2.0 (22H, m), 2.1-2.5 (1H, m), 2.6-2.9 (4H, m), 3.3-3.55 (2H, m), 4.35-4.55 (1H, m), 4.7-4.9 (2H, m), 6.1-6.4 (1H, m), 6.65-6.9 (1H, m) 7.05-7.4 (10H, m) 9.05-9.30 (1H, m).

[4-(N-Hydroxyamino)-2,R,S-Isobutylsuccinyl]-L-β-cyclohexylalanine-N-(2-phenylethyl) amide The mixture of diastereoisomers N was dissolved in degassed MeOH (20 ml) and hydrogenolysed using 5% Pd-C and hydrogen gas. After 1 hour at RT the catalyst was filtered off and the product purified on RPHPLC using 0.1%TFA/H₂O→0.1%TFA/CH₃CN (43:57) isocratically. Peak 1 (elution time 11.2 min) and Peak 2

(elution time 14 min) was collected and dried to give 64 mg and 56 mg of the title isomers respectively.

PEAK 1 $^1$HNMR (CD$_3$OD) 0.8–1.0 (8H, m), 1.05–1.75 (14H, m), 2.1–2.4 (2H, m), 2.7–2.85 (3H, m), 3.35–3.50 (2H. m), 4.30 (1H, t, J=6 Hz), 7.05–7.3 (5H, m)

PEAK 2 $^1$HNMR (CD$_3$OD) 0.8–1.8 (22H, m), 2.05–2.20 (1H, m), 2.35–2.5 (1H, m), 2.7–2.9 (3H, m), 3.35–3.5 (2H, m), 4.30–4.40 (1H, m), 7.1–7.35 (5H, m)

The following compounds of Examples 3–14 were prepared in a similar manner to the compounds of Examples 1 and 2 using the appropriate analogous starting materials

EXAMPLE 3

[4-(Hydroxyamino)-2R-phenylethylsuccinyl]-L-$\beta$-cyclohexylalanine-N(2-phenylethyl) amide The title compound was prepared following the general teaching of Example 1.

$^1$HNMR CD$_3$OD 7.1–7.3 (10H, mult, Ar); 4.35 (1H, mult, NCHCO); 3.35 (2H, mult, CH$_2$N); 2.20–280 (7H, mult, CHCO+CH$_2$Ar); 0.70–1.80 (15H, multi, CHC)

EXAMPLE 4

[4-(N-Hydroxyamino)-2R-phenylpropylsuccinyl]-L-$\beta$-cyclohexylalanine-N-(2-phenylethyl) amide The title compound was prepared following the general teaching of Example 2.

$^1$HNMR CD$_3$OD 7.05–7.30 (10H, mult, Ar); 4.30 (1H, t, NCHCO) 3.30–3.50 (2H, mult, CH$_2$N); 2.70 (2H, t, CH$_2$Ar); 2.10–2.60 (5H, mult, CHCO+CH$_2$Ar); 0.80–1.70 (17H, mult, CHC)

EXAMPLE 5

[4-(N-Hydroxyamino)-2 R-phenylpropylsuccinyl]-L-$\beta$-cyclohexylalanine-N-[2-(N,N-dimethylamine]ethyl amide The title compound was prepared following the general teaching of Example 2.

$^1$HNMR (CD$_3$OD) $\delta$ 0.75–1.85 (17H, m), 2.28 (1H, dd, HZ), 2.48–2.75 (4H, m), 2.9 (6H, s), 3.21–3.40 (2H, m), 3.55–3.70 (2H, m), 4.15 (1H, dd, HWCHCO) 7.10–7.30 (5H, m, Ar)

EXAMPLE 6

[4-(N-Hydroxyamino)-2R-phenylpropylsuccinyl]-L-$\beta$-cyclohexylalanine-N-(2-(p-sulphonamidophenyl) ethyl) amide.

The title compound was prepared following the general teaching of Example 2

$^1$HNMR (CD$_3$OD) $\delta$ 0.7–1.75 (17H, m), 2.1–2.2 (1H, m), 2.3–2.4 (1H, m), 2.45–2.85 (5H, m) 3.2–3.4 (2H, m) 4.2–4.35 (1H, m), 7.05–7.20 (5H, m), 7.35 (2H, d, J=7H), 7.85 (2H, d, J=7 HZ).

EXAMPLE 7

[4-(N-Hydroxyamino)-2R-phenylpropylsuccinyl]-L-$\beta$-cyclohexylalanine-N-[2-(p-sulphonylphenyl)ethyl] amide.

The title compound was prepared following the general teaching of Example 2.

$^1$HNMR (CD$_3$OD) $\delta$ 0.75–1.8 (17H, m), 2.15–2.95 (7H, m), 3.20–3.60 (2H, m), 4.25–4.7 (1H, m), 7.05–7.35 (7H, m), 7.75 (2H, d, J=7 Hz).

EXAMPLE 8

[4-(N-Hydroxyamino)-2R-phenylpropylsuccinyl]-L-$\beta$-cyclohexylalanine-N-[2-(2-pyridyl) ethyl] amide The title compound was prepared following the general teaching of Example 2.

TFA salt $^1$HNMR (CD$_3$OD) $\delta$ 8.7 (1H, d), 8.40 (1H, t), 7.90 (1H, d), 7.80 (1H, t), 4.10 (1H, dd), 3.65 (2H, t), 3.15–3.40 (2H, mult), 2.70 (1H, mult), 2.30–2.50 (2H, 2dd), 0.80–1.80 (22H, mul,t)

EXAMPLE 9

[4-(N-Hydroxyamino)-2R-N-pentylsuccinyl]-L-$\beta$-cyclohexylalanine-N-(2-phenylethyl) amide The title compound was prepared following the general teaching of Example 2.

$^1$HNMR (CD$_3$OD) $\delta$ 7.15–7.35 (5H, mult), 4.35 (1H,t), 3.30–3.50 (2H, mult), 2.80 (2H, t), 2.70 (1H, mult), 2.15–2.40 (2H, 2dd), 0.90–1.80 (24H, mult).

EXAMPLE 10

[4-(N-Hydroxyamino)-2R-isoamylsuccinyl]-L-$\beta$-cyclohexylalanine-N-(2-phenylethyl) amide The title compound was prepared following the general teaching of Example 2.

$^1$HNMR (CD$_3$OD) $\delta$ 7.15–7.35 (5H, mult), 4.30 (1H, t), 3.30–3.50 (2H, mult), 2.80 (2H, t), 2.70 (1H, mult), 2.15–2.40 (2H, 2dd), 0.90–1.80 (24H, mult).

EXAMPLE 11

[4-(N-Hydroxyamino)-2R-phenylbutylsuccinyl]-L-$\beta$-cyclohexylalanine-N-(2-phenylethyl) amide The title compound was prepared following the general teaching of Example 2.

$^1$HNMR (CD$_3$OD) $\delta$ 7.2–7.4 (10H, mult, Ar), 4.35 (1H, mult, NCHCO), 3.30–3.45 (2H, mult, CH$_2$N), 2.20–2.90 (7H, mult, CH$_2$Ar+CH$_2$CO), 0.85–1.80 (19H, mult, CH$_2$C)

EXAMPLE 12

[4-(N-Hydroxyamino)-2R-phenylpropylsuccinyl]-L-$\beta$-cyclohexylalanine-N-[3(4-morpholinyl)propyl] amide The title compound was prepared following the general teaching of Example 2.

$^1$HNMR (CD$_3$OD) $\delta$ 7.15–7.35 (5H, mult, Ar), 4.15 (1H, t, NCHCO), 3.70–4.10 (4H, mult, CH$_2$O), 3.0–3.50 (8H, mult, CH$_2$N), 2.20–2.80 (5H, mult, CH$_2$CO+CH$_2$Ar+CHCO), 0.90–2.0 (19H, mult, CH$_2$C).

EXAMPLE 13

[4-(N-Hydroxyamino)-2R-phenylpropylsuccinyl]-L-$\beta$-cyclohexylalanine-N-[$\beta$-alanine methyl ester]amide.

The title compound was prepared following the general teaching of Example 2.

$^1$H NMR (CD$_3$OD) $\delta$ 0.9–1.9 (mult, 17H), 2.2–2.4 (2dd, 2H), 2.5–2.9 (mult, 5H), 3.3 (mult, 2H), 3.6 (s, 3H), 4.3 (m, 1H), 7.2 (mult, 5H)

EXAMPLE 14

[4-(N-Hydroxyamino)-2R-phenylpropylsuccinyl]-L-$\beta$-cyclohexylalanine-N-[$\beta$-alanine] amide The title compound was prepared from the methyl ester (329 mg, 0.67 mmol) of Example 13 by dissolution in methanol (10 ml) and addition of lithium hydroxide (74 mg, 1.76 mmol) in water (5 ml) dropwise with stirring. This was allowed to stir overnight. The reaction was concentration in vacuo to about ¼ volume. A partition was obtained between 10% citric acid and chloroform.

The organic layer was separated and evaporated to give a white solid (314 mg).

The product was purified on RP HPLC using TFA/H₂O/CH₃CN (starting with 0.1:80:20 and ending with 0.1:20:80 over 20 min) to give the title compound (150 mg).

¹H NMR (CD₃OD) δ 0.9-2.8 (mult, 17H), 2.15-2.4 (2dd, 2H), 2.5-2.8 (mult, 5H), 3.35 (mult, 3H), 4.35 (dd, 1H), 7.2 (mult, 5H)

EXAMPLE 15

Methyl-(2-methoxycarbonyl)-5-phenylpentanoate (I)

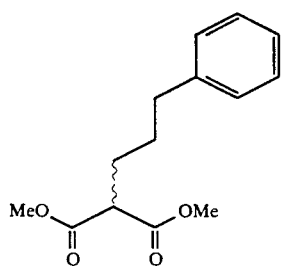

(I)

Sodium methoxide was prepared by adding sodium metal (3.66 g, 159 mmol) to dry methanol (200 ml) under nitrogen. Upon dissolution dimethyl malonate (20 g, 17.3 ml, 151 mmol) was added dropwise followed by dropwise addition of 1-bromo-3-phenylpropane (30.1 g, 23 ml, 151 mmol). The mixture was refluxed for 18 hours, cooled and partitioned between phosphate buffer (pH=6.5) and diethyl ether. The organic layer was separated, dried (MgSO₄) and concentrated in vacuo. Purification on silica gel (Merck 9385), eluting with Et₂O/hexane (25:75) gave the compound I as a colourless oil (23.26 g, 62%).

¹H NMR (CDCl₃) δ 7.2-7.45 (5H, m), 3.78 (6H, s), 3.45 (1H, t), 2.70 (2H, t), 1.95-2.15 (2H, m), 1.65-1.85 (2H, m).

tert -Butyl-2(R,S)-bromo-5-phenylpentanoate (II)

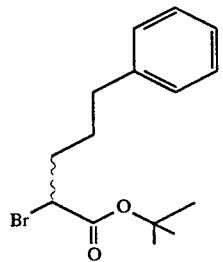

(II)

Methyl-(2-methoxycarbonyl)-5-phenylpentanoate (I), (8.43 g, 33.7 mmol) was dissolved in MeOH (40 ml) and NaOH (3.37 g, 84.25 mmoL) dissolved in H₂O (10 ml) was added. The mixture was refluxed for 18 hours, cooled, concentrated in vacuo and addified to pH=1 using concentrated HCl. The aqueous solution was extracted with Et₂O (3×50 ml), dried (MgSO₄) and concentrated in vacuo to give a white solid (6.3 g). The white solid was dissolved in diethyl ether and bromine (1.5 ml, 28.2 mmol) added dropwise. Decolourization occurred after 10 minutes and the reaction was stirred at room temperature for a further 2 hours. Water was added carefully and the product extracted into Et₂O (3×100 ml), dried (MgSO₄) and concentrated in vacuo. The residue was dissolved in xylene and refluxed for 24 hours. The solvent was removed under reduced pressure and the residue taken up in CH₂Cl₂ (50 ml) and the solution was cooled to −40° C. Isobutene was condensed until the reaction volume doubled and concentrated H₂SO₄ (1 ml) was added dropwise. The reaction mixture was allowed to warm to room temperature overnight and the mixture poured into aqueous NaHCO₃ (10%). The organic layer separated and dried (MgSO₄). Purification on silica gel (Merck 9385) eluting with Et₂O/hexane (2.5:97.5) gave the compound II (4.0 g) as a solid.

¹H NMR (CDCl₃) δ 7.1-7.3 (5H, m), 4.10 (1H, t), 2.65 (2H, t), 1.9-2.15 (2H, m), 1.55-1.90 (2H, m), 1.45 (9H, s).

Benzyl-[2-benzyloxycarbonyl-3(R,S)-tert-butoxycarbonyl]-6-phenylhexanoate (III)

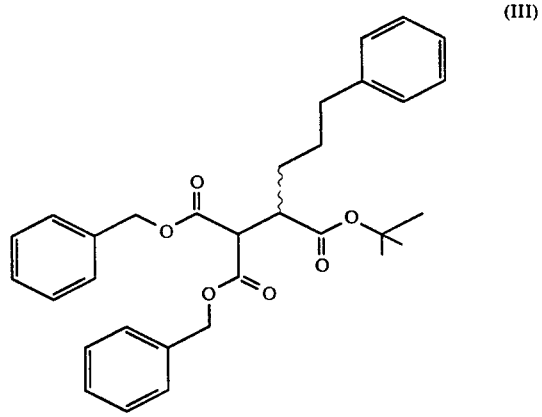

(III)

Dibenzyl malonate (3.53 g, 12.5 mmol) was dissolved in DMF (20 ml) and cooled to 0° C. Potassium t-butoxide (1.39 g, 12.5 mmol) was added as a solid and upon dissolution, tert-butyl-2(R,S)-bromo-5-phenylpentanoate (II) (3.90 g, 12.5 mmol) in dry DMF (10 ml) was added dropwise over 30 minutes. The reaction was allowed to warm up to room temperature overnight and partitioned between EtOAC and saturated aqueous ammonium chloride. The organic layer was separated, dried (MgSO₄) and concentrated in vacuo. The residue was purified on silica gel (Merck 9385) eluting with 10→15% Et₂O in hexane to give the compound (III) (4.9 g).

¹H NMR (CDCl₃) δ 7.05-7.55 (15H, m), 5.1-5.2 (4H, m), 3.8 (1H, d), 3.05-3.15 (1H, m), 2.40-2.70 (2H, m), 1.45-1.80 (4H, m), 1.35 (9H, s).

Benzyl-[2-benzyloxycarbonyl-3(R,S)-(3-phenylpropyl)-]succinate (IV)

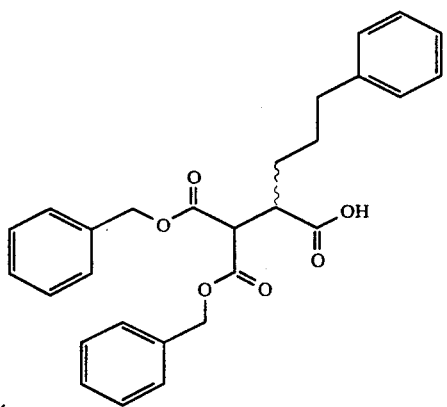

Benzyl-[2-benzyloxycarbonyl-3(R,S)-tert-butoxycarbonyl]-6-phenylhexanoate (III) (4.9 g, 9.5 mmol) was dissolved in TFA/H$_2$O (10 ml, 9.5:0.5 v/v) and allowed to stand at 4° C. for 2 days. The TFA was removed under reduced pressure and the residue partitioned between CH$_2$Cl$_2$ and H$_2$O. The organic layer was separated, dried (MgSO$_4$) and concentrated in vacuo to give the compound (IV) (4.36 g) as a white solid.

$^1$H NMR (CDCl$_3$) δ 7.0–7.35 (15H, m), 5.05–5.20 (4H, m), 3.82 (1H, d), 3.15–3.28 (1H, m), 2.38–2.58 (2H, m), 1.48–1.80 (4H, m).

[4-Benzyloxy-3-benzyloxycarbonyl-2(R,S)-(3-phenylpropyl)succinyl]-L-β-cyclohexylalanine-(N-2-phenylethyl) amide (V)

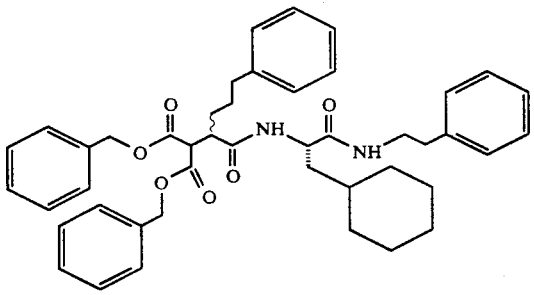

Benzyl-[2-benzyloxycarbonyl-3(R,S)-(3-phenylpropyl)] succinate (IV) (2.3 g, 5 mmoL) was dissolved in dry DMF (20 ml). To this was added HOBT (0.75 g, 5 mmoL), N-methylmorpholine (55 μl, 5 mmoL) and L-β-cyclohexylalanine-(N-2-phenylethyl) amide (J) (1.37 g, 5 mmoL). The solution was cooled to 0° C. and DCCl (1.03 g, 5 mmoL) in dry DMF (10 ml) was added over a ten minute period. The reaction mixture was allowed to warm up to RT overnight, poured into EtOAc and washed with 10% w/v citric acid. The organic layer was separated, washed with aqueous NaHCO$_3$ (10% w/v) and dried (MgSO$_4$). The solvent was removed in vacuo to give an oily solid (3.4 g) which was purified on silica gel (Merck 9385) using MeOH/CH$_2$Cl$_2$ (0.5→1% MeOH) to give the compound V as a glass.

$^1$H NMR (CDCl$_3$) δ 7.0–7.55 (20H, m), 6.2 (1H, t), 6.0 (1H, d), 5.0–5.2 (4H, m), 4.3–4.55 (1H, m), 3.8–3.94 (1H, m), 3.2–3.6 (2H, m), 2.7–2.9 (3H, m), 2.4–2.55 (2H, m), 0.7–2.0 (17H, m).

[4-Hydroxy-2(R)-(3-phenylpropyl)succinnyl]-L-β-cyclohexylalanine-(N-2-phenylethyl) amide (VI)

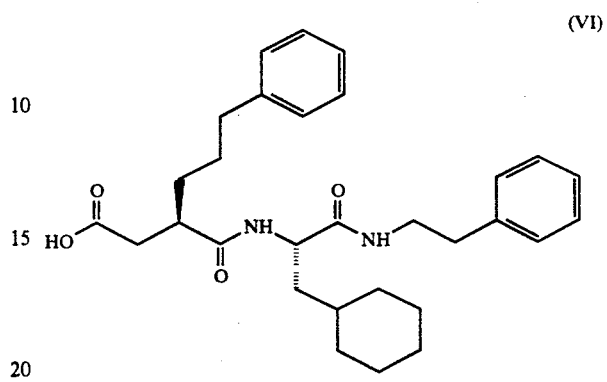

[4-Benzyloxy-3-benzyloxycarbonyl-2(R,S)-(3-phenylpropyl)succinyl]-L-β-cyclohexylalanine-(N-2-phenylethyl) amide (V) (340 mg) was dissolved in MeOH and treated with hydrogen over Pd on C for 18 hours. The catalyst was filtered and the solvent removed under vacuum. The residue was taken up in neat xylene and heated under reflux for 15 minutes. The xylene was removed under vacuum to give a yellow gum which was purified on RPHLC using TFA/H$_2$O/CH$_3$CN (starting with 0.1:50:50 ending with 0.1:0:100 over 20 minutes) to give the compound (VI) PEAK 1 43.5 mg and the other diastereoisomer PEAK 2 (47 mg)

$^1$H NMR PEAK 1 (CD$_3$OD) δ 7.1–7.3 (10H, m), 4.32 (1H, dd), 3.25–3.45 (2H, m); 2.25–2.80 (7H, m), 0.8–1.8 (17H, m).

$^1$H NMR PEAK 2 (CD$_3$OD) δ 7.1–7.25 (10H, m), 4.25–4.3 (1H, m), 3.25–3.50 (2H, m), 2.25–2.95 (&H, m), 0.7–1.85 (17H,.m).

The following compounds of Examples 16–20 were prepared following the procedures of Example 15 and using the appropriate analogous starting materials.

EXAMPLE 16

[4-Hydroxy-2(R)-(3-phenylpropyl)succinyl]-L-β-cyclohexylalanine-β-alanine methyl ester

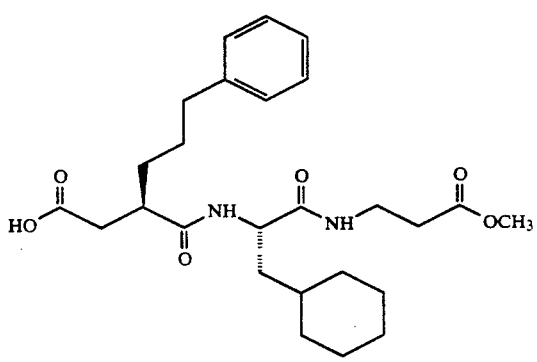

$^1$H NMR (CD$_3$OD) δ 7.05–7.30 (5H, m), 4.35 (1H, t), 3.60 (3H, s), 3.20–3.45 (2H, m), 2.40–2.85 (7H, m), 0.85–1.95 (17H, m).

EXAMPLE 17

[4-Hydroxy-2(R)-(3-phenylpropyl)succinyl]-L-β-cyclohexylalanine-β-alanine

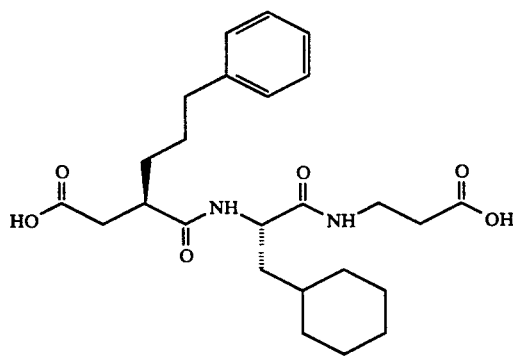

¹H NMR (CD₃OD) δ 7.10-7.30 (5H, m), 4.35 (1H, dd), 3.35-3.50 (2H, m), 2.32-2.85 (7H, m), 0.75-1.85 (17H, m)

EXAMPLE 18

[4-Hydroxy-2(R)-(3-phenylpropyl)succinyl]-L-β-cyclohexylalanine-β-alanine amide

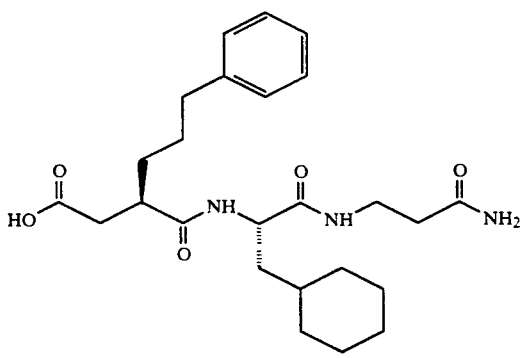

¹H NMR (CD₃OD) δ 7.10-7.30 (5H, m), 4.35 (1H, dd), 3.35-3.45 (2H, m), 2.55-2.85 (4H, m), 2.45-2.55 (3H, m), 0.78-1.8 (17H, m)

EXAMPLE 19

[4-Hydroxy-2(R)-isobutylsuccinyl]-L-β-cyclohexylalanine-(N-2-phenylethyl) amide

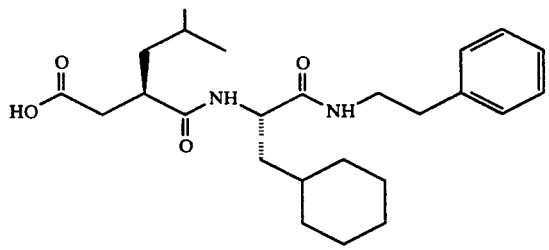

¹H NMR (CD₃OD) δ 7.10-7.60 (5H, m), 4.45 (1H, dd), 3.30-3.80 (2H, m), 2.35-3.10 (5H, m), 0.75-1.95 (22H, m).

EXAMPLE 20

[4-Hydroxy-2(R)-isoamylsuccinyl]-L-β-cyclohexylalanine-(N-2-phenylethyl) amide

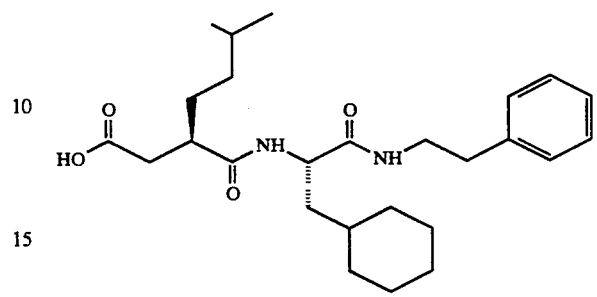

¹H NMR (CD₃OD) δ 7.15-7.45 (5H, m), 4.60 (1H, dd), 3.50-3.80 (2H, m), 2.90 (2H, t), 2.80 (1H, dd), 2.55 (1H, dd), 0.90-1.90 (24H, m).

EXAMPLE 21

(a)

(S)-3[1-oxo-5-(4-methylpheny)lpentyl]-4-(phenylmethyl)-2-oxazolidinone (I)

BuLi (1.6M solution in hexanes, 4.4 mmol, 2.75 ml, 1,2 equiv.) was added dropwise to a solution of (S)-4-(phenylmethyl)-2-oxazolidinone (3.64 mmol, 0.64 g) in THF (15 ml) at −78° C., under N₂ atmosphere. The orange solution was stirred for 30 mins at −78° C. and then a solution of p-toylvalerylchloride (4.06 mmol, 0.86 g) in THF (5 ml) was added dropwise. The reaction mixture was stirred at −78° C. for 2 hrs before quenching at −78° C. with a solution of brine 10% aqueous HCl (1:1, 10 ml). On warming to ambient temperature the reaction mixture was partioned betwen ethyl acetate and water. The aqueous layer was separated and extracted twice with ethyl acetate. The combined organic layers were washed once with brine, once with sodium bicarbonate solution, dried over MgSO4. The solvent was removed under vacuum to give a brown oil which was purified on silica gel (Merck 9385) eluting with 20% EtOAc/hexane to give the compound (I) as a slightly yellow oil (0.65 g, 51%).

¹HNMR (CDCl₃) δ 1.63 (m, 4H), 2.31 (s, 3H), 2.62 (m, 2H) 2.75 (dd, 1H), 2.89-2.98 (m, 2H), 3.26 (dd, 1H), 4.12-4.18 (m, 2H), 4.61-4.67 (m, 1H), 7.17-7.36 (m, 9H)

(b)

3-[1-oxo-2(R)-(t-butylacetyl)-5-(4-methylphenyl)pentyl]-4-(S)-phenylmethyl-2-oxazolidinone (2)

A solution of the oxazolidinone (I) (0.65 g, 1.85 mmol) in THF (10 ml) was added to a solution of sodium bistrimethylsilylazide (1M Solution in THF, 2.6 mmol, 2.6 ml, 1.4 equiv.) in THF (10 ml) at −78° C. under nitrogen. The reaction mixture was stirred at this temperature for 1 hr and then +−butylbromoacetate (5.6 mmol, 1.08 g, 0.90 ml, 3 equiv) was added dropwise. The reaction was allowed to warm to −20° C. and stirred at this temperature for 4 hours. The reaction was quenched at −78° C. with a solution of brine 10% HCl acid (1:1, 10 ml). The mixture was partitioned between EtOAC and water. The aqueous layer was separated and extracted twice with EtOAC. The combined EtOAC layers were washed once with brine and once with NaHCO₃ solution, dried over MgSO4 and the solvent removed to give a yellow oil, which was purified an Silica gel (Merck 9385) eluting with 20% EtOAc/hexane to give the compound (2) 0.57 g, 66%.

¹HNMR (CDCl₃) δ 1.42 (s, 9H), 1.57-1.62 (m, 2H), 2.30 (s, 3H), 2.41-2.85 (m, 5H), 3.33 (dd, 1H), 4.10-4.25 (m, 1H), 7.01-7.09 (m, 4H), 7.22-7.37 (m, 5H)

(c) 2-(R)-[3-(4-methylphenyl)propyl]succinic acid-4-t-butyl monoester (3)

A solution of the oxazolidinone (2) (0.57 g, 1.23 mmol) in THF/water (4:1, 25 ml) was cooled in an ice bath and treated with hydrogen peroxide solution (27.5 wt %, 4.9 mmol, 0.56 ml, 4 equiv.). The mixture was stirred for a few minutes and then heated dropwise with a solution of lithium hydroxide monohydrate (1.23 mmol, 52 mg, 1.0 equiv) in water (5 ml). The reaction was stirred for 1.1/2 hrs then treated with a 10% aqueous solution of sodium sulphite (5 ml). The reaction mixture was adjusted to pH 12-13 with 1M NaOH and then partitioned between dichloromethane and water. The aqueous layer was separated and acidified with 10% HCl. The aqueous layer was extracted three times with EtOAc. The combined organic layers were washed once with brine, once with NaHCO₃ solution and dried over MgSO4 and the solvent removed to give the compound (3) as a yellowish oil 0.18 g, 48%, which was used without further purification.

¹H NMR (CDCl₃) δ 1.43 (s, 9H), 1.51-1.79 (m, 4H), 2.32 (s, 3H), 2.37 (dd, 1H), 2.82 (M, 1H) 7.03-7.12 (m, 4H)

(d) [4-t-butoxy-2(R)-[3-(4-methylphenylpropyl]succinyl]-L-β-cyclohexylalanine-N-(2-phenylethyl)amide (4)

A solution of the acid (3) (0.18 g, 0.59 mmol, 1.05 equiv.) in THF (10 ml) was treated with N-methyl morpholine (0.62 mmol, 62.2 mg, 67.7 μl) and cooled to −20° C. under N₂. The mixture was then treated with ethyl chlorofomate (0.59 mmol, 64.1 mg, 56.5 μl) and stirred at −20° C. for 1 hr during which time a white precipitate formed. After this time a solution of L-β-cyclohexylalanine-N-(2-phenylethyl) amide (154 mg, 0.56 mmol) in THF (5 ml) was added dropwise and the reaction allowed to warm to ambient temperature overnight. The reaction mixture was partitioned between ethyl acetate and water. The aqueous layer was separated and extracted twice with EtOAC. The combined EtOAc layers were washed once with 10% HCl, once with NaHCO₃ and once with brine, dried over MqSO4 and the solvent removed under vacuum to give a yellow oil, which was purified on silica gel (Merck 9385) eluting with 1% MeOH CH₂Cl₂ to give 0.16 g of the ester (4) as a slightly yellow oil.

¹HNMR (CDCl₃) δ 0.77-1.67 (m, 18H), 1.42 (s, 9H), 2.26 (s, 3H), 2.32 (d, 1H), 2.76 (t, 2H), 3.23-3.56 (m, 2H), 4.37 (m, 1H), 6.17 (d, 1H), 6.41 (t, 1H), 6.98-7.37 (m, 9H)

EXAMPLE 22

[4-Hydroxy-2-(R)-[3(4-methylphenyl)propyl]succinyl]-L-β-cyclohexylalanine-N-(2-phenylethyl) amide The t-butylester of Example 21 (0.16 g, 0.28 m mol) was treated with water (0.5 ml) and TFA (2.5 ml) and allowed to stand overnight (@ 18 hr). The volatiles were removed under vacuum to give a yellow oil which solidified on standing. Trituration with diisopropyl ether gave the title compound as powedery solid 122 mg, 86%

¹HNMR (CD₃OD) δ 0.77-1.78 (16H, m) 2.19 (3H, s) 2.33-2.80 (7H, m) 3.26-3.39 (3H, m) 4.34 (1H, dd), 6.94-7.32 (9H, m)

The compounds of Examples 23-25 were prepared in a similar manner to the acid of Example 22 from analogous starting materials.

EXAMPLE 23

[4-Hydroxy-2R-phenylpropylsuccinyl]-L-β-cyclohexylalanine-N-[2-(benzyloxycarbamoyl)ethyl] amide ¹HNMR (CD₃OD) δ7.37 (s), 7.36 (5H, s), 7.07-7.34 (m, 5H), 5.13 (s, 2H), 4.33 (1H, dd) 3.25 (4H, br, d), 2.75 (2H, m), 2.60 (2H, t), 2.44 (m, 1H), 0.8-1.9 (17h, m)

EXAMPLE 24

[4-Hydroxy-2R-phenylpropylsuccinyl]-L-βcyclohexylalanine-N-[2-(p-sulphonamidophenyl) ethyl] amide ¹HNMR, (CD₃OD) δ 7.7 (2H, d), 7.35 (2H, d), 7.05-7.35 (7H, m), 4.35 (1H, dd), 3.35-3.45 (2H, m), 2.70-2.85 (2H, m), 2.50-270 (2H, m), 2.38 (1H, dd), 0.75-1.85 (17H, m)

EXAMPLE 25

[4-Hydroxy-2R-phenylpropylsuccinyl]-L-β-cyclohexylalanylglycine methyl ester

¹HNMR (CD₃OD) δ 7.1-7.4 (5H, m), 4.45 (1H, dd), 3.95 (1H, d), 3.80 (1H, d) 3.70 (3H, s), 2.70-2.85 (1H, m), 2.55-2.70 (3H, m), 2.38 (1H, dd), 0.85-1.85 (17H, m).

EXAMPLE A

The activity and selectivity of the compounds of the invention may be determined as described below.

All enzyme assays to determine Ki values were performed using the peptide substrate Dnp-Pro-Leu-Gly-Leu-Trp-Ala-D-Arg-NH₂. (M. Sharon Stock and Robert D. Gray. JBC 264, 4277-81, 1989). The enzymes cleave at the Gly-Leu bond which can be followed fluorimetrically by measuring the increase in Trp fluorescence emission associated with the removal of the quenching dinitrophenol (Dnp) group.

Essentially, enzyme (e.g. gelatinase, stromelysin, collagenase) at 0.08-2 nM; a range of inhibitor concentrations (0.1-50×Ki) and substrate (approx. 20 μm) are incubated overnight in 0.1M Tris/HCl buffer, pH 7.5, containing 0.1M NaCl, 10 mM CaCl₂ and 0.05%. Brij 35 at either room temperature or 37° C. depending on the enzyme. The reaction is stopped by adjusting the pH to 4 using 0.1M sodium acetate buffer and the fluorescence read at an excitation wavelength of 280 nm and emission wavelength of 346 nm.

$K_i$ values can be established using the equation for tight-being inhibition:

$$V_i = \frac{V_o}{2[E]} \left( \sqrt{(K_{i(app)} + [I])^2 + 2(K_{i(app)} - [I])[E] + [E]^2} - (K_{i(app)} + [I] - [E]) \right)$$

where $V_o$ is the initial rate of reaction in the absence of inhibitor, $V_i$ is the initial rate in the presence of inhibitor, [E] is the total enzyme concentration and [I] the total inhibitor concentration in the reaction mixture.

For stromelysin and collagenase, $K_i(app)$ was assumed to approximate to the true $K_i$ as $[S]<<K_m$ for the substrate hydrolysis. For gelatinase the $K_i$ was determined by performing the analyses at several substrate concentrations. A plot of $K_i(app)$ vs. $[S]$ then gave the true $K_i$ as the value of the y-axis intercept.

The following results were obtained with compounds according to the invention.

| Compound of Example No. | Ki (nM) | | |
|---|---|---|---|
| | Collagenase | Stromelysin-1 | Gelatinase-72KD |
| 6 | 150 | 5.92 | 0.025 |
| 12 | 210 | 24.8 | 0.14 |
| 15 | 45 μM | 842 | 21 |
| 16 | 57 μM | 1.47 μM | 6 |

We claim:
1. A compound of formula (I):

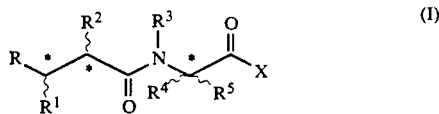

wherein R represents a —CONHOH,
R$^1$ represents a hydrogen atom or an unsubstituted or substituted alkyl, alkenyl, aryl, aralkyl, heteroaralkyl or heteroarylthioalkyl group;
R$^2$ represents an unsubstituted or substituted alkyl, alkenyl, cycloalkyl, cycloalkylalkyl, aryl, aralkyl, aralkoxy, or aralkylthio group, or an amino (—NH$_2$), substituted amino, carboxyl (—CO$_2$H) or esterified carboxyl group;
R$^3$ represents a hydrogen atom or an alkyl group;
R$^4$ represents a hydrogen atom or an alkyl group;
R$^5$ represents a group —[Alk]$_n$R$^6$ where Alk is an alkyl or alkenyl group optionally interrupted by one or more —O— or —S— atoms or —N(R$^7$)— groups, n is zero or an integer 1, and R$^6$ is an unsubstituted or substituted cycloalkyl or cycloalkenyl group;
X represents an amino (—NH$_2$), or substituted amino, and a salt, solvate or hydrates thereof.

2. A compound according to claim 1 wherein R$^1$, R$^3$ and R$^4$ is each a hydrogen atom.

3. A compound according to any of claim 1 wherein R$^2$ is an unsubstituted or substituted alkyl, cycloalkyl, cycloalkylalkyl, aryl, aralkoxy or aralkylthio group.

4. A compound according to claim 1 wherein R$^5$ is a AlkR$^6$ group where Alk is a C$_{1-6}$alkyl and R$^6$ is a cycloalkyl or cycloalkenyl group.

5. A compound of formula (Ia)

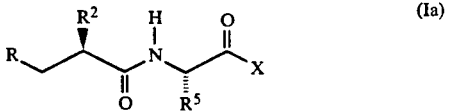

wherein R represents a —CONHOH;
R$^2$ represents an unsubstituted or substituted alkyl, alkenyl, cycloalkyl, cycloalkylalkyl, aryl, aralkyl, aralkoxy, or aralkylthio group, or an amino (—NH$_2$), substituted amino, carboxyl (—CO$_2$H) or esterified carboxyl group;

R$^5$ represents a group —[Alk]$_n$R$^6$ where Alk is an alkyl or alkenyl group optionally interrupted by one or more —O— or —S— atoms or —N(R$^7$)— groups [where R$^7$ is a hydrogen atom or a C$_{1-6}$alkyl group], n is zero or an integer 1, and R$^6$ is an unsubstituted or substituted cycloalkyl or cycloalkenyl group;
X represents an amino (—NH$_2$), or substituted amino; and a salt, solvate or hydrate thereof 6. A compound according to claim 5 wherein R$^2$ represents an unsubstituted or substituted alkyl, alkenyl, cycloalkyl, cycloalkylalkyl, aryl, aralkoxy or aralkylthio group;
R$^5$ represents a group —AlkR$^6$, where Alk is a C$_{1-6}$alkyl group and R$^6$ is a cycloalkyl or cycloalkenyl group;
X is an amino (—NH$_2$) or substituted amino group; and a salt, solvate or hydrate thereof.

7. A compound according to claim 6 where R$^5$ represents a cyclohexylC$_{1-6}$alkyl group.

8. A compound according to claim 7 where R$^5$ represents a cyclohexylmethyl group.

9. A compound according to claim 6 wherein R$^2$ is an unsubstituted or substituted phenylC$_{2-6}$alkyl group.

10. A compound according to claim 9 wherein R$^2$ represents an unsubstituted or substituted phenylpropyl group.

11. A compound according to claim 1; which is
[4-(N-Hydroxyamino)-2(R)-cyclohexylmethylsuccinyl]-L-β-cyclohexylalanine-N-(2-phenylethyl) amide,
[4-N-(Hydroxyamino)-2R-isobutylsuccinyl]-L-β-cyclohexylalanine-N-(2-phenylethyl) amide,
[4-(N-hydroxyamino)-2R-phenylpropylsuccinyl]-L-β-cyclohexylalanine-N-(2-phenylethyl) amide,
[4-(N-Hydroxyamino)-2R-phenylpropylsuccinyl]-L-β-cyclohexylalanine-N-[2-(N,N-dimethylamino]ethyl amide,
[4-(N-Hydroxyamino)-2R-phenylpropylsuccinyl]-L-β-cyclohexylalanine-N-(2-(p-sulphonamidophenyl)ethyl) amide,
[4-(N-Hydroxyamino)-2R-phenylpropylsuccinyl]-L-β-cyclohexylalanine-N-(2-(p-sulphonylphenyl) ethyl) amide,
[4-(N-Hydroxyamino)-2R-phenylpropylsuccinyl]-L-β-cyclohexylalanine-N-[2-(2-pyridyl)ethyl] amide,
[4-(N-Hydroxyamino)-2R-pentylsuccinyl]-L-β-cyclohexylalanine-N-(2-phenylethyl) amide,
[4-(N-Hydroxyamino)-2R-isoamylsuccinyl]-L-β-cyclohexylalanine-N-(2-phenylethyl) amide,
[4-(N-Hydroxyamino)-2R-phenylbutylsuccinyl]-L-β-cyclohexylalanine-N-(2-phenylethyl) amide,
[4-(N-Hydroxyamino)-2R-phenylpropylsuccinyl]-L-β-cyclohexylalanine-N-[3-(4-morpholinyl)propyl] amide,
[4-(N-Hydroxyamino)-2R-phenylpropylsuccinyl]-L-β-cyclohexylalanine-N-[β-alanine]amide,
[4-(N-Hydroxyamino)-2R-isobutylsuccinyl]-L-β-cyclohexylalanine amide,
[4-(N-Hydroxyamino)-2R-(3-phenylpropyl)succinyl]-L-β-cyclohexylalanine amide,
[4-(N-Hydroxyamino)-2R-(3-phenylbutyl)succinyl]-L-β-cyclohexylalanine amide, and a salt, solvate or hydrate thereof.

12. A pharmaceutical composition comprising a compound according to any one of claim 1 and a pharmaceutically acceptable diluent, carrier or excipient.

* * * * *

UNITED STATES PATENT AND TRADEMARK OFFICE
CERTIFICATE OF CORRECTION

PATENT NO. : 5,300,501
DATED : April 5, 1994
INVENTOR(S) : John R. PORTER, et al.

It is certified that error appears in the above-indentified patent and that said Letters Patent is hereby corrected as shown below:

Column 31, line 42, claim 1, folowing the word "groups" insert -- [where $R^7$ is a hydrogen atom or a $C_{1-6}$ alkyl group ]--.

Signed and Sealed this

Fifteenth Day of November, 1994

BRUCE LEHMAN

Attest:

Attesting Officer

Commissioner of Patents and Trademarks